United States Patent
Robinson et al.

(10) Patent No.: US 11,977,277 B2
(45) Date of Patent: *May 7, 2024

(54) LENS FOR EYEWEAR AND OTHER HEADWORN SUPPORTS HAVING IMPROVED OPTICS

(71) Applicant: Oakley, Inc., Foothill Ranch, CA (US)

(72) Inventors: David Robinson, Mission Viejo, CA (US); Jason Belbey, Fullerton, CA (US); Brock Scott McCabe, Laguna Niguel, CA (US)

(73) Assignee: Oakley, Inc., Foothill Ranch, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/728,722

(22) Filed: Apr. 25, 2022

(65) Prior Publication Data
US 2022/0260853 A1 Aug. 18, 2022

Related U.S. Application Data

(63) Continuation of application No. 16/523,927, filed on Jul. 26, 2019, now Pat. No. 11,314,105.

(Continued)

(51) Int. Cl.
*G02C 7/02* (2006.01)
*A61F 9/04* (2006.01)
(Continued)

(52) U.S. Cl.
CPC .............. *G02C 7/021* (2013.01); *A61F 9/045* (2013.01); *G02C 5/001* (2013.01); *B29L 2011/0025* (2013.01); *G02B 3/06* (2013.01)

(58) Field of Classification Search
CPC .............. G02C 7/02; A61F 9/02–9/029; A61F 9/04–9/045
(Continued)

(56) References Cited

U.S. PATENT DOCUMENTS 4,279,480 A * 7/1981 Bettiol .................... G02C 7/02
  359/718
4,561,736 A * 12/1985 Furter ..................... G02C 7/02
  251/159

(Continued)

FOREIGN PATENT DOCUMENTS

| CN | 102782565 A | 11/2012 |
| EP | 0809126 | 3/2003 |

(Continued)

OTHER PUBLICATIONS

Zhu, Jun et al., "Design method of surface contour for a freeform lens with wide linear field-of-view," Optics Express 21(22) (Oct. 24, 2013), pp. 26080-26092; 13 pages.

(Continued)

*Primary Examiner* — Zachary W Wilkes
(74) *Attorney, Agent, or Firm* — Sterne, Kessler, Goldstein & Fox P.L.L.C.

(57) ABSTRACT

A lens is provided that has an improved optical configuration in order to provide enhanced off-axis optical performance by tending to reduce, eliminate, or minimize first order optical distortion. Embodiments may be used in non-corrective or corrective unitary or dual lens eyewear, for example in combination with a frame to support the lens in a path of a straight ahead line of sight forming a center axis of an eye of a typical wearer. The lens may comprise a lens body. The lens body may comprise a surface having a spheric, toric, cylindrical or freeform geometry and another surface having a freeform geometry. A lens thickness is defined between the surfaces. A prismatic power of the lens is improved, particularly for off-axis viewing angles.

20 Claims, 14 Drawing Sheets

Related U.S. Application Data

(60) Provisional application No. 62/734,032, filed on Sep. 20, 2018, provisional application No. 62/703,850, filed on Jul. 26, 2018.

(51) Int. Cl.
*G02C 5/00* (2006.01)
*B29L 11/00* (2006.01)
*G02B 3/06* (2006.01)

(58) Field of Classification Search
USPC .............. 351/159.71–159.72, 159.37–159.38
See application file for complete search history.

(56) References Cited

U.S. PATENT DOCUMENTS

| | | | |
|---|---|---|---|
| 4,859,048 A | 8/1989 | Jannard | |
| 5,604,547 A * | 2/1997 | Davis | G02C 7/02 351/44 |
| 5,969,789 A | 10/1999 | Houston et al. | |
| 6,010,217 A | 1/2000 | Houston | |
| 6,038,705 A | 3/2000 | Jarvis | |
| 6,056,401 A | 5/2000 | Shirayanagi | |
| 6,086,204 A | 7/2000 | Magnante | |
| 6,089,713 A | 7/2000 | Hof et al. | |
| 6,176,577 B1 * | 1/2001 | Monnoyeur | G02C 7/02 351/159.2 |
| 6,334,681 B1 | 1/2002 | Perrott | |
| 6,364,481 B1 * | 4/2002 | O'Connor | G02C 7/02 351/44 |
| 6,715,150 B1 | 4/2004 | Potin | |
| 7,147,325 B2 * | 12/2006 | Gotou | G02C 7/028 351/159.1 |
| 7,419,261 B2 | 9/2008 | Dumange et al. | |
| 7,460,985 B2 | 12/2008 | Benitez et al. | |
| 7,717,559 B2 | 5/2010 | Ito et al. | |
| 8,035,898 B2 | 10/2011 | Miñano et al. | |
| 8,403,503 B1 | 3/2013 | Geng | |
| 9,529,213 B2 | 12/2016 | Fonte et al. | |
| 11,314,105 B2 * | 4/2022 | Robinson | G02C 7/021 |
| 2002/0008844 A1 | 1/2002 | Copeland | |
| 2003/0169397 A1 | 9/2003 | Reichow et al. | |
| 2005/0122470 A1 * | 6/2005 | Perrott | G02C 7/02 351/159.01 |
| 2007/0121220 A1 | 5/2007 | Tsai et al. | |
| 2011/0205626 A1 | 8/2011 | Saylor et al. | |
| 2012/0081800 A1 | 4/2012 | Cheng et al. | |
| 2012/0120366 A1 | 5/2012 | Clerc et al. | |
| 2014/0222182 A1 | 8/2014 | Currie et al. | |
| 2014/0253874 A1 | 9/2014 | Spratt et al. | |
| 2015/0094993 A1 | 4/2015 | Zhu et al. | |
| 2015/0127304 A1 | 5/2015 | Cassarly | |
| 2016/0033791 A1 | 2/2016 | Kozu | |
| 2016/0299360 A1 | 10/2016 | Fonte et al. | |
| 2017/0017095 A1 | 1/2017 | Fricker et al. | |
| 2019/0384061 A1 * | 12/2019 | Arora | G02B 27/0172 |
| 2020/0033632 A1 * | 1/2020 | Robinson | G02C 7/021 |

FOREIGN PATENT DOCUMENTS

| | | |
|---|---|---|
| EP | 1 582 909 A1 | 10/2005 |
| EP | 1 657 587 A1 | 5/2006 |
| JP | H11509448 A | 8/1999 |
| JP | 2001510905 A | 8/2001 |
| JP | 2008-026776 A | 2/2008 |
| JP | 2012-234036 A | 11/2012 |
| JP | 2013-033298 A | 2/2013 |
| JP | 2013-518301 A | 5/2013 |
| TW | M247852 U | 10/2004 |
| WO | WO 98/30930 A1 | 7/1998 |
| WO | WO 9904307 | 1/1999 |
| WO | WO 2017/054878 A1 | 4/2017 |
| WO | WO 2017/062813 A1 | 4/2017 |

OTHER PUBLICATIONS

ANSI/ISEA Z87.1-2015, "American National Standard for Occupational and Educational Personal Eye and Face Protection Devices," Approved May 28, 2015; 64 pages.

Nike Vaporwing Elite, accessed Nov. 22, 2019 from https://www.nikevision.com/us/en/products/detail/nike-vaporwing-elite/#EV0913_100; 3 pages.

International Search Report and Written Opinion, dated Oct. 24, 2019 in Related PCT Application No. PCT/US2019/043797; 16 pages.

International Preliminary Report on Patentability directed to related International Patent Application No. PCT/US2019/043797, dated Jan. 26, 2021; 10 pages.

Keating, M. P. "Oblique Central Refraction in Spherocylindrical Corrections with Both Faceform and Pantoscopic Tilt," Optometry & Vision Science, vol. 72, No. 4, Apr. 1, 1995; pp. 258-265.

* cited by examiner

LENS FOR EYEWEAR AND OTHER HEADWORN SUPPORTS HAVING IMPROVED OPTICS

CROSS-REFERENCE TO RELATED APPLICATIONS

This application is a continuation of U.S. application Ser. No. 16/523,927, which was filed on Jul. 26, 2019 and claims the benefit of U.S. applications 62/703,850, which was filed on Jul. 26, 2018, and 62/734,032, which was filed on Sep. 20, 2018, each of which is incorporated by reference herein in its entirety.

FIELD

Embodiments of the present invention relate generally to a lens for eyewear, and more particularly to a uniquely configured lens having enhanced off-axis optical performance resulting in the reduction, minimization, or elimination of prismatic shift, also sometimes referred to as prismatic effect, power, aberration, or distortion. Such lenses may be used in, for example, active sports or as fashion sunglasses. Embodiments of these eyewear designs accomplish a variety of functional advantages, such as maximizing interception of peripheral light, reducing optical distortion and increasing the wearer's comfort level, compared to legacy eyewear.

BACKGROUND

Although unitary lens systems provide a full side-to-side range of vision and good lateral eye protection, the current state of the art still contends with optical distortion problems. In a unitary lens system, for example, the angle of incidence of a line from the wearer's eye to the posterior lens surface changes as the wearer's sight line moves to any angle with respect to a straight-ahead line of sight, referred to herein as an "off-axis" direction. The off-axis direction may be, for example, a lateral direction, a vertical direction, or combination thereof. This results in disparate refraction between light entering closer to the front of the lens and peripheral light entering at the off-axis portions of the lens. The disclosure in U.S. Pat. No. 4,859,048 is one example of efforts to address this source of prismatic distortion, in this case, by tapering the thickness of the lens from the medial portion toward the lateral edge. Another example is U.S. Pat. No. 5,969,789.

Dual lens systems have been developed in which the lateral edge of each lens curves rearwardly from the frontal plane, and around the side of the wearer's head to provide a lateral wrap similar to that achieved by the high wrap unitary lens systems. Although the dual lens eyeglasses with significant wrap provide some lateral eye protection, the lens curvature generally introduces measurable prismatic distortion through the wearer's angular range of vision. This is particularly pronounced in lenses comprising high index of refraction materials. In addition, although high base curvatures (e.g. base 6 or higher) are sometimes desirable to optimize wrap while maintaining a low profile, such lenses employ a turned surface geometry and have not been optically optimal in the past due to the relatively high level of prismatic distortion at off-axis viewing angles.

SUMMARY

In an embodiment, a lens for use in non-corrective dual lens eyewear or headgear, in combination with a frame to support the lens in a path of a straight ahead line of sight forming a center axis of one eye of a typical wearer, comprises a lens body. In an embodiment, the lens body comprises a front surface having a spheric, toric, cylindrical or freeform geometry. In an embodiment, the lens body comprises a rear surface having a freeform geometry. In an embodiment, a lens thickness is defined between the front surface and the rear surface. In an embodiment, a viewing axis extends from the one eye and the center axis at an angle from the center axis away from the typical wearer's nose measured along a horizontal meridian of the rear surface. In an embodiment, each point along the horizontal meridian of the rear surface is associated with an angle of the viewing axis where the viewing axis intersects the each point along the horizontal meridian of the rear surface. In an embodiment, a prismatic power of the lens does not exceed approximately 0.25 diopter throughout points along the horizontal meridian of the rear surface, associated with angles of the viewing axis approximately 30 degrees or less.

In an embodiment, a unitary lens for use in non-corrective eyewear or headgear, in combination with a frame to support the lens in the path of a left and right straight ahead line of sight respectively forming a left center axis of the left eye and a right center axis of the right eye of a typical user, comprises a lens body. In an embodiment, the lens body comprises a front surface having a spheric, toric, cylindrical, or freeform geometry. In an embodiment, the lens body comprises a rear surface having a freeform geometry. In an embodiment, a lens thickness is defined between the front surface and the rear surface. In an embodiment, a left viewing axis extends from the left eye and the left center axis at an angle to the left center axis away from the typical wearer's nose measured along a horizontal meridian of the rear surface. In an embodiment, each of first points along the horizontal meridian of the rear surface is associated with an angle of the left viewing axis where the left viewing axis intersects the each of the first points along the horizontal meridian of the rear surface. In an embodiment, a prismatic power of the unitary lens does not exceed approximately 0.23 diopter throughout the first points along the horizontal meridian of the rear surface associated with angles of the left viewing axis approximately 30 degrees or less.

In an embodiment, a method for designing a lens for non-corrective eyewear or headgear comprises generating a point mesh of an initial front surface of the lens. In an embodiment, the method comprises generating a point mesh of a freeform rear surface of the lens based on the initial front surface. In an embodiment, points of the point mesh of the freeform rear surface correspond with points of the point mesh of the initial front surface. In an embodiment, the method comprises determining a forward viewing axis relative to the lens based on an as worn position of the lens relative to a typical wearer's eye. In an embodiment, the method comprises determining a seed point on the initial front surface. In an embodiment, the seed point is a starting reference for subsequent iterative calculations. In an embodiment, the method comprises assigning an initial thickness at the seed point. In an embodiment, the method comprises calculating a surface normal of a first point on the freeform rear surface corresponding to the seed point. In an embodiment, the method comprises placing the first point on the freeform rear surface according to the initial thickness and a refraction of a light ray intersecting the seed point from the surface normal to the freeform rear surface. In an embodiment, the method comprises calculating surface normals at points adjacent to the first point on the freeform rear surface corresponding to points in the point mesh of the initial front surface adjacent to the seed point. In an embodiment, the method comprises calculating thicknesses for the points adjacent to the seed point using an optimization algorithm. In an embodiment, the optimization algorithm comprises calculations of refraction of light rays based on the calculated surface normals at the points adjacent to the first point on the freeform rear surface. In an embodiment, the method comprises placing points adjacent to the first point on the freeform rear surface according to the calculated thicknesses for the points adjacent to the seed point. In an embodiment, the method comprises placing additional points on the freeform rear surface with iterative calculations of surface normals and thicknesses of points adjacent to placed points.

Methods of designing a lens according to an embodiment of the present invention are also disclosed.

Further features and advantages of the present invention will become apparent from the detailed description of preferred embodiments which follows, when considered together with the attached claims and drawings.

BRIEF DESCRIPTION OF THE DRAWINGS/FIGURES

DETAILED DESCRIPTION

Figure 1:
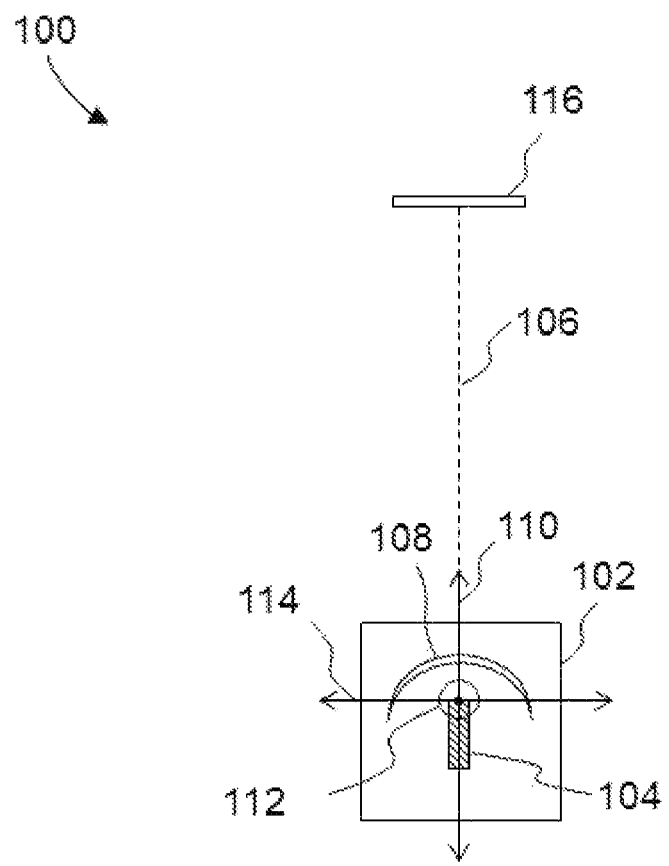
FIG. 1 is a schematic illustration of a prismatic power measurement apparatus, according to an example embodiment.

Although the preferred embodiments will be discussed below in terms of lenses having a "freeform" geometry for front and/or rear surfaces (e.g., a geometry that is not spheric, toric, flat, or cylindrical), it is to be appreciated that the invention may also be applicable to lenses having a combination of a freeform surface and a turned surface. Additionally, it is to be appreciated that embodiments of the present disclosure have application to lenses of many front elevational shapes and orientations in the as-worn position beyond those illustrated herein. Further, the term "true angle optical effect" refers to a correction to off-axis light rays that minimizes optical distortion from the perspective of a wearer as compared to standard turned surface lenses.

The embodiment(s) described, and references in the specification to "one embodiment," "an embodiment," "a preferred embodiment" and the like, indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

The term "lens" as used herein is used to broadly refer to an optical component. For example, eyeglass/sunglass lenses, vision shields, visors, and the like are included in the term "lens" or "lens for eyewear." The term "non-corrective" as used herein indicates a lack of optical power as understood for prescription lenses.

Spatially relative terms, such as "beneath," "below," "lower," "above," "on," "upper" and the like, may be used herein for ease of description to describe one element or feature's relationship to another element(s) or feature(s) as illustrated in the figures. Spatially relative terms are intended to encompass different orientations of an apparatus in addition to or instead of an orientation depicted in the figures. For example, an apparatus may be otherwise oriented and spatially relative descriptors used herein may likewise be interpreted accordingly.

The terms "approximate," "approximately," and the like as used herein indicates the value of a given quantity that may vary based on a particular technology. Based on the particular technology, the term "approximate" and the like may indicate a value of a given quantity that varies within, for example, 0-10% of the value (e.g., ±0.5%, ±5%, or ±10% of the value).

The terms "typical wearer," "typical user," and the like as used herein may refer to a median user in general, a median user according to a demographic, or a user having physical dimensions conforming to a standard or a well-known database of human measurements. For example, a typical eyewear wearer may be one having physical dimensions that conform to European Standards (EN), American National Standards Institute (ANSI), or anthropometric surveys, among others.

Additionally, although particular embodiments may be disclosed or shown in the context of particular types of eyewear, such as unitary lens eyeglasses, dual lens eyeglasses, eyeglasses having partial, full, or no orbitals, goggles, sunglasses, eyewear with earstems, eyewear with partial earstems, eyewear without earstems, and the like, it is to be appreciated that embodiments of the present disclosure may be used in any type of headworn support. For example, lens embodiments may be integrated into or attached to an item of headgear, such as a bicycle, skateboarding, snow, flight, sport, or other type of helmet with a vision shield, a visor, a hat, a headband, face mask, balaclava, breaching shield, or any other any headworn article that may support one or more lenses in the wearer's field of view. In some embodiments, the lens may be detachable from the headworn article so that the lens may be removed or replaced without damaging the headworn article.

Some method and system embodiments of the present disclosure may be implemented in hardware, firmware, software, or any combination thereof. Embodiments of the present disclosure may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, and/or instructions may be described herein as performing certain actions. However, it should be appreciated that such descriptions are merely for convenience and that such actions in fact result from computing devices, processors, controllers, or other devices executing the firmware, software, routines, instructions, etc.

Despite the many advances of eyewear lenses, there is a continuing need for a lens having excellent optical qualities and providing reduced optical distortion while at the same time providing a configuration that allows for adequate ventilation, maximum comfort and safety to the wearer, and/or attachment to specific headgear. Further, there is a need for a lens for use in eyewear which can intercept light over essentially the full angular range of vision while at the same time minimizing optical distortion throughout that range.

Before describing such embodiments in more detail, however, it is instructive to present example metrics in which embodiments of the present disclosure may be characterized and implemented.

Example Optical Performance Measurements

FIG. 1 is a schematic illustration of an example prismatic power measurement apparatus 100. In an embodiment, prismatic power measurement apparatus 100 comprises a sample mounting stage 102 and a collimated radiation source 104 (e.g., a laser) configured to output a collimated radiation beam 106. In an embodiment, sample mounting stage 102 is configured to support a device-under-test (DUT) 108 (e.g., a lens, eyewear, or visor). In an embodiment, sample mounting stage 102 is configured to be adjustable, with adjustments comprising: translations along or parallel to a horizontal axis 114, a vertical axis 112, and a straight ahead line of sight axis 110; and rotations about or relative to horizontal axis 110, vertical axis 112, and straight ahead line of sight axis 114. In an embodiment, collimated radiation source 104 is structurally independent from sample mounting stage 102 such that collimated radiation source 104 remains stationary when sample mounting stage 102 is adjusted. It is to be appreciated that horizontal axis 114 and vertical axis 112 are perpendicular and parallel, respectively, to a medial line through a body of a potential user wearing DUT 108, and that horizontal axis 114 and vertical axis 112 are both perpendicular to straight ahead line of sight axis 110. It is also to be appreciated that DUT 108, being a lens, when worn by a wearer, has a surface that faces toward the user, commonly called a rear surface, and a surface that faces away from the user, commonly called a front surface.

In an embodiment, measurement apparatus 100 comprises a measurement target 116. Measurement target 116 comprises concentric circular markings (not shown) configured to quantify prismatic powers of DUT 108 by measuring the deflection of the collimated beam 106 transmitted through DUT 108 for different positions and rotations of DUT 108. In this embodiment, measurement target 116 is configured to have a fixed position and orientation relative to collimated radiation source 104. The measurements of deflections of collimated beam 106 transmitted through DUT 108 are made relative to a zero-deflection condition in which DUT 108 is absent.

Figure 2:
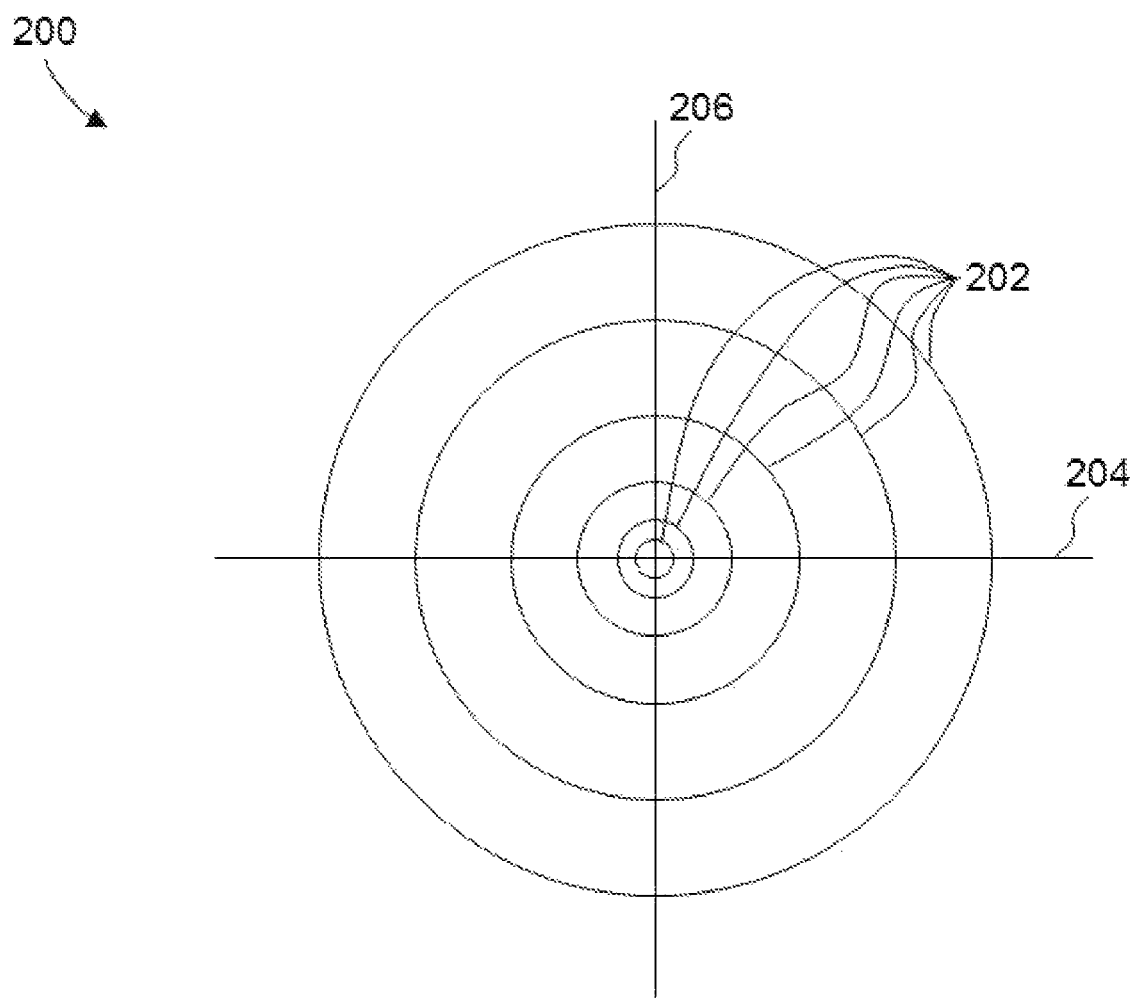
FIG. 2 is a schematic illustration of a target used in a prismatic power measurement apparatus, according to an example embodiment.

FIG. 2 is a schematic illustration of a target 200 used in a prismatic power measurement apparatus, according to an example embodiment. In an embodiment, target 200 comprises concentric circular markers 202 having different radii. In an embodiment, target 200 comprises a horizontal axis marker 204 and a vertical axis marker 204 that intersect at a center of concentric circular markers 202.

It is to be appreciated that measurements of prismatic power (e.g., the power induced by the lens causing displacement of an image) may also be calculated via computer simulations to corroborate the measurements and/or to test new lens designs before production. Other physical testing methods may also be used, such as an ANSI-certified test method.

The tables below show measured and simulated prismatic power of various legacy lenses, having various base curves, as compared to inventive lenses possessing a "true angle optics" geometry as described with respect to embodiments of the present disclosure. Legacy lenses as referred to herein include conventional eyewear which in some instances may be corrected for forward-viewing only. The measurements and simulations quantify deviations of light rays directed toward a typical user's eye and passing through a lens. For example, Table 1 shows an actual measurement performed on an example Legacy Lens 1 (a 4-base lens for dual lens eyewear) quantifying a displacement, induced by Legacy Lens 1, of an image. The data column labeled 'viewing axis angle' are off-axis viewing directions, measured in degrees with respect to a straight ahead line of sight, toward a horizontal lateral periphery (Horizontal) and a top periphery (Vertical). For the horizontal viewing axis angle, a positive angle indicates a viewing direction directed toward the user's temple nearest to the eye being measured, e.g., the right eye angled toward the right temple or the left eye angled toward the left temple. Conversely, a negative horizontal viewing axis angle indicates a viewing direction of an eye that is directed toward the user's nose. The measurements and simulations referenced herein were performed from the perspective of the right eye of a user. A person skilled in the art will recognize that left eye measurements and simulations would yield substantially similar and mirrored results for a typical user having a substantially symmetric facial structure. Viewing axis angles in all tables herein are within the field of view of the lens, which varies by lens. For example, Legacy Lenses 1-4 have viewing clearances up to approximately 40-55 degrees toward the temple closest to the eye being measured/simulated before a frame supporting the lens occludes vision, while the vision shield may potentially allow for horizontal viewing up to the eye's peripheral limit of approximately 105 degrees, though here it was measured up to approximately 90 degrees. Quantification of viewing axis angles toward a user's nose (negative angles), e.g., Legacy Lens 2, do not take into account occlusion by the user's nose, but a person skilled in the art will recognize that viewing clearance toward a user's nose are likely to be limited by nose occlusion rather than a frame supporting the lens. It is to be appreciated that the true angle optics method described in embodiments of the present disclosure for correcting prismatic distortion may also or instead be applied to viewing angles toward a top and bottom periphery of a lens, or any off-axis angle (e.g., any combination of horizontal and vertical viewing angles at non-zero degrees with respect to a straight ahead line of sight—that is, any combination of X and Y displacements). Table 1 shows a prismatic power of an example Legacy Lens 1 measured in diopters, where a horizontal and vertical displacement of an image caused by Legacy Lens 1 are quantified as a prismatic power X and Y, respectively, with values closer to 0 being preferred. The total prismatic power of Legacy Lens 1, R, is calculated as $R=\sqrt{X^2+Y^2}$. Table 1 also shows an alternative metric to prismatic power, and that is a horizontal component of angular displacement of an incoming light ray caused by the lens, $\theta_X$, and a vertical component of angular displacement of an incoming light ray caused by the lens, $\theta_Y$, both measured in degrees, with values closer to 0 being preferred. Table 1 shows a third alternative metric to quantify a displacement of an image caused by the lens, and that is as an apparent horizontal displacement of an object placed at approximately 100 yards from the wearer, $D_X$, and an apparent vertical displacement of an object placed at approximately 100 yards from a wearer, $D_Y$, with values closer to 0 being preferred. The total apparent displacement of an object placed at approximately 100 yards from a wearer, $D_R$, is calculated as $D_R=\sqrt{D_X^2+D_Y^2}$.

All data tables in the present disclosure will use the organizational scheme, labels, and calculations for derived data employed in Table 1.

Provided in Table 2 is a simulation of a redesigned Legacy Lens 1 employing an embodiment of the present disclosure on the rear surface to compare with the measurement results of the original Legacy Lens in Table 1. The results in Table 2 show a marked improvement of simulated optical performance (e.g., a reduction of overall prismatic power) when applying the true angle optics method of the present disclosure to the rear surface of the lens. The greatest reduction of total prismatic power, from 0.61 to 0.36 diopter (approximately halved), occurs at the highest measured horizontal viewing axis angle of 55 degrees.

Table 3 shows a simulated prismatic power of an example Legacy Lens 2, which has a toric 4×6 geometry (vertical approximately 4-base and horizontal approximately 6-base) and Table 4 shows a simulated prismatic power of a redesigned Legacy Lens 2 employing an embodiment of the present disclosure on the rear surface. Similar to the data of Legacy Lens 1, the total prismatic power of redesigned Legacy Lens 2 is reduced compared to original Legacy Lens 2, from 0.91 to 0.52 diopter, at the highest measured horizontal viewing axis angle of 50 degrees. Table 3 is based on a 4×6 unitary lens, but a dual lens 4×6 toric design may be similarly optimized to achieve improvements similar to that of higher base lenses (e.g., the performance of the such toric design can exhibit the same or similar performance as shown in Table 8 for a lens with 8.75 base).

Regarding higher base curves, Table 5 shows a measured prismatic power of an example Legacy Lens 3, which has a high wrap, e.g., greater than approximately 6.5-base, and is a unitary lens for wraparound eyewear, and Table 6 shows a measured prismatic power of an example Legacy Lens 4, which has a base curvature of 8.75 and is a lens for dual lens eyewear. Table 7 shows simulated prismatic power of Legacy Lens 4 to corroborate a good agreement between simulations and actual measurements. When an embodiment of the present disclosure is applied to Legacy Lens 4, the prismatic power of Legacy Lens 4 is drastically reduced, which is shown in Table 8. Table 8 shows, that the total prismatic power of redesigned Legacy Lens 4 is reduced from 1.02 to 0.21 diopter compared to original Legacy Lens 4, at the highest measured horizontal viewing axis angle of 50 degrees. This is approximately a 5-factor reduction of total prismatic power.

Another improvement of peripheral viewing fidelity was measured on an actual, freeform vision shield for use in protective headgear (e.g., football helmet) fabricated with an embodiment of the present disclosure. The vision shield is entirely freeform, having a freeform front surface and corresponding freeform rear surface and resulting in what is referred to herein as a True Angle Optical profile. The measurement data for the prismatic power of the vision shield is shown in Table 9. The vision shield maintains a total prismatic power not exceeding 0.25 diopter throughout all horizontal viewing axis angles up to 90 degrees.

TABLE 1

Legacy Lens 1: 4-Base Legacy Lens of Dual Lens System (Actual Measurement)

| Viewing Axis Angle (degrees) | | Prismatic Power (diopters) | | | Angular Displacement (degrees) | | Apparent Displacement of Object at 100 Yards (inches) | | |
|---|---|---|---|---|---|---|---|---|---|
| Horizontal | Vertical | X | Y | R | $\theta_X$ | $\theta_Y$ | $D_X$ | $D_Y$ | $D_R$ |
| 0 | 0 | −0.030 | −0.030 | 0.04 | −0.0160 | −0.0160 | −2.97 | −2.97 | −1.00 |
| 5 | 0 | 0.030 | 0.030 | 0.04 | 0.0160 | 0.0160 | 2.97 | 2.97 | 1.00 |
| 10 | 0 | 0.080 | −0.030 | 0.09 | 0.0426 | −0.0160 | 7.93 | −2.97 | 2.68 |
| 15 | 0 | 0.100 | −0.030 | 0.10 | 0.0532 | −0.0160 | 9.91 | −2.97 | 3.34 |
| 20 | 0 | 0.120 | −0.060 | 0.13 | 0.0639 | −0.0319 | 11.89 | −5.95 | 4.01 |
| 25 | 0 | 0.180 | −0.060 | 0.19 | 0.0958 | −0.0319 | 17.84 | −5.95 | 6.02 |
| 30 | 0 | 0.240 | −0.080 | 0.25 | 0.1278 | −0.0426 | 23.79 | −7.93 | 8.03 |
| 35 | 0 | 0.300 | −0.090 | 0.31 | 0.1597 | −0.0479 | 29.74 | −8.92 | 10.03 |
| 40 | 0 | 0.360 | −0.090 | 0.37 | 0.1916 | −0.0479 | 35.68 | −8.92 | 12.04 |
| 45 | 0 | 0.400 | −0.060 | 0.40 | 0.2129 | −0.0319 | 39.65 | −5.95 | 13.38 |
| 50 | 0 | 0.500 | −0.060 | 0.50 | 0.2662 | −0.0319 | 49.56 | −5.95 | 16.72 |
| 55 | 0 | 0.600 | −0.120 | 0.61 | 0.3194 | −0.0639 | 59.47 | −11.89 | 20.07 |

TABLE 2

Redesigned Legacy Lens 1, Having a Freeform Rear Surface Resulting in a True Angle Optical Profile (Simulation)

| Viewing Axis Angle (degrees) | | Prismatic Power (diopters) | | | Angular Displacement (degrees) | | Apparent Displacement of Object at 100 Yards (inches) | | |
|---|---|---|---|---|---|---|---|---|---|
| Horizontal | Vertical | X | Y | R | $\theta_X$ | $\theta_Y$ | $D_X$ | $D_Y$ | $D_R$ |
| 0 | 0 | 0.000 | −0.015 | 0.02 | 0.0000 | −0.0080 | 0.00 | −0.50 | 0.50 |
| 5 | 0 | 0.016 | 0.015 | 0.02 | 0.0085 | 0.0080 | 0.54 | 0.50 | 0.73 |
| 10 | 0 | 0.024 | −0.015 | 0.03 | 0.0128 | −0.0080 | 0.80 | −0.50 | 0.95 |
| 15 | 0 | 0.052 | −0.015 | 0.05 | 0.0277 | −0.0080 | 1.74 | −0.50 | 1.81 |
| 20 | 0 | 0.075 | −0.020 | 0.08 | 0.0399 | −0.0106 | 2.51 | −0.67 | 2.60 |
| 25 | 0 | 0.101 | −0.030 | 0.11 | 0.0538 | −0.0160 | 3.38 | −1.00 | 3.52 |
| 30 | 0 | 0.130 | −0.040 | 0.14 | 0.0692 | −0.0213 | 4.35 | −1.34 | 4.55 |
| 35 | 0 | 0.162 | −0.045 | 0.17 | 0.0862 | −0.0240 | 5.42 | −1.51 | 5.62 |
| 40 | 0 | 0.203 | −0.045 | 0.21 | 0.1081 | −0.0240 | 6.79 | −1.51 | 6.95 |
| 45 | 0 | 0.251 | −0.030 | 0.25 | 0.1336 | −0.0160 | 8.40 | −1.00 | 8.46 |
| 50 | 0 | 0.304 | −0.030 | 0.31 | 0.1618 | −0.0160 | 10.17 | −1.00 | 10.22 |
| 55 | 0 | 0.352 | −0.060 | 0.36 | 0.1874 | −0.0319 | 11.77 | −2.01 | 11.94 |

TABLE 3

Legacy Lens 2: Toric 4 × 6 Legacy Lens (Simulation)

| Viewing Axis Angle (degrees) | | Prismatic Power (diopters) | | | Angular Displacement (degrees) | | Apparent Displacement of Object at 100 Yards (inches) | | |
|---|---|---|---|---|---|---|---|---|---|
| Horizontal | Vertical | X | Y | R | $\theta_X$ | $\theta_Y$ | $D_X$ | $D_Y$ | $D_R$ |
| −50 | 0 | −0.910 | 0.000 | 0.91 | −0.4844 | 0.0000 | −30.44 | 0.00 | 30.44 |
| −40 | 0 | −0.660 | 0.000 | 0.66 | −0.3513 | 0.0000 | −22.08 | 0.00 | 22.08 |
| −30 | 0 | −0.460 | 0.000 | 0.46 | −0.2449 | 0.0000 | −15.39 | 0.00 | 15.39 |
| −20 | 0 | −0.290 | 0.000 | 0.29 | −0.1544 | 0.0000 | −9.70 | 0.00 | 9.70 |
| −10 | 0 | −0.140 | 0.000 | 0.14 | −0.0745 | 0.0000 | −4.68 | 0.00 | 4.68 |
| 0 | 0 | 0.000 | 0.000 | 0.00 | 0.0000 | 0.0000 | 0.00 | 0.00 | 0.00 |
| 10 | 0 | 0.140 | 0.000 | 0.14 | 0.0745 | 0.0000 | 4.68 | 0.00 | 4.68 |
| 20 | 0 | 0.290 | 0.000 | 0.29 | 0.1544 | 0.0000 | 9.70 | 0.00 | 9.70 |
| 30 | 0 | 0.460 | 0.000 | 0.46 | 0.2449 | 0.0000 | 15.39 | 0.00 | 15.39 |
| 40 | 0 | 0.680 | 0.000 | 0.68 | 0.3620 | 0.0000 | 22.75 | 0.00 | 22.75 |
| 50 | 0 | 1.020 | 0.000 | 1.02 | 0.5430 | 0.0000 | 34.12 | 0.00 | 34.12 |

TABLE 4

Redesigned Legacy Lens 2, Having a Freeform Rear Surface Resulting in a True Angle Optical Profile (Simulation)

| Viewing Axis Angle (degrees) | | Prismatic Power (diopters) | | | Angular Displacement (degrees) | | Apparent Displacement of Object at 100 Yards (inches) | | |
|---|---|---|---|---|---|---|---|---|---|
| Horizontal | Vertical | X | Y | R | $\theta_X$ | $\theta_Y$ | $D_X$ | $D_Y$ | $D_R$ |
| −50 | 0 | −0.420 | 0.000 | 0.42 | −0.2236 | 0.0000 | −14.05 | 0.00 | 14.05 |
| −40 | 0 | −0.370 | 0.000 | 0.37 | −0.1970 | 0.0000 | −12.38 | 0.00 | 12.38 |
| −30 | 0 | −0.275 | 0.000 | 0.28 | −0.1464 | 0.0000 | −9.20 | 0.00 | 9.20 |
| −20 | 0 | −0.175 | 0.000 | 0.18 | −0.0932 | 0.0000 | −5.85 | 0.00 | 5.85 |
| −10 | 0 | −0.116 | 0.000 | 0.12 | −0.0618 | 0.0000 | −3.88 | 0.00 | 3.88 |
| 0 | 0 | 0.000 | 0.000 | 0.00 | 0.0000 | 0.0000 | 0.00 | 0.00 | 0.00 |
| 10 | 0 | 0.124 | 0.000 | 0.12 | 0.0660 | 0.0000 | 4.15 | 0.00 | 4.15 |
| 20 | 0 | 0.194 | 0.000 | 0.19 | 0.1033 | 0.0000 | 6.49 | 0.00 | 6.49 |
| 30 | 0 | 0.270 | 0.000 | 0.27 | 0.1437 | 0.0000 | 9.03 | 0.00 | 9.03 |
| 40 | 0 | 0.370 | 0.000 | 0.37 | 0.1970 | 0.0000 | 12.38 | 0.00 | 12.38 |
| 50 | 0 | 0.421 | 0.000 | 0.42 | 0.2241 | 0.0000 | 14.08 | 0.00 | 14.08 |

TABLE 5

Legacy Lens 3: High Wrap Legacy Unitary Lens (Actual Measurement)

| Viewing Axis Angle (degrees) | | Prismatic Power (diopters) | | | Angular Displacement (degrees) | | Apparent Displacement of Object at 100 Yards (inches) | | |
|---|---|---|---|---|---|---|---|---|---|
| Horizontal | Vertical | X | Y | R | $\theta_X$ | $\theta_Y$ | $D_X$ | $D_Y$ | $D_R$ |
| 0 | 0 | 0.030 | 0.100 | 0.10 | 0.0160 | 0.0532 | 1.00 | 3.34 | 3.49 |
| 5 | 0 | −0.030 | 0.100 | 0.10 | −0.0160 | 0.0532 | −1.00 | 3.34 | 3.49 |
| 10 | 0 | −0.090 | 0.100 | 0.13 | −0.0479 | 0.0532 | −3.01 | 3.34 | 4.50 |
| 15 | 0 | −0.190 | 0.120 | 0.22 | −0.1011 | 0.0639 | −6.36 | 4.01 | 7.52 |
| 20 | 0 | −0.200 | 0.110 | 0.23 | −0.1065 | 0.0586 | −6.69 | 3.68 | 7.63 |
| 25 | 0 | −0.290 | 0.100 | 0.31 | −0.1544 | 0.0532 | −9.70 | 3.34 | 10.26 |
| 30 | 0 | −0.320 | 0.100 | 0.34 | −0.1704 | 0.0532 | −10.70 | 3.34 | 11.21 |
| 35 | 0 | −0.380 | 0.100 | 0.39 | −0.2023 | 0.0532 | −12.71 | 3.34 | 13.14 |
| 40 | 0 | −0.450 | 0.100 | 0.46 | −0.2396 | 0.0532 | −15.05 | 3.34 | 15.42 |
| 45 | 0 | −0.500 | 0.090 | 0.51 | −0.2662 | 0.0479 | −16.72 | 3.01 | 16.99 |
| 50 | 0 | −0.580 | 0.100 | 0.59 | −0.3088 | 0.0532 | −19.40 | 3.34 | 19.69 |
| 55 | 0 | −0.620 | 0.110 | 0.63 | −0.3301 | 0.0586 | −20.74 | 3.68 | 21.06 |

TABLE 6

Legacy Lens 4: 8.75-Base Legacy Lens of Dual Lens System (Actual Measurement)

| Viewing Axis Angle (degrees) | | Prismatic Power (diopters) | | | Angular Displacement (degrees) | | Apparent Displacement of Object at 100 Yards (inches) | | |
|---|---|---|---|---|---|---|---|---|---|
| Horizontal | Vertical | X | Y | R | $\theta_X$ | $\theta_Y$ | $D_X$ | $D_Y$ | $D_R$ |
| 0 | 0 | 0.060 | 0.000 | 0.06 | 0.0319 | 0.0000 | 2.01 | 0.00 | 2.01 |
| 5 | 0 | 0.160 | 0.000 | 0.16 | 0.0852 | 0.0000 | 5.35 | 0.00 | 5.35 |
| 10 | 0 | 0.260 | 0.020 | 0.26 | 0.1384 | 0.0106 | 8.70 | 0.67 | 8.72 |
| 15 | 0 | 0.330 | 0.045 | 0.33 | 0.1757 | 0.0240 | 11.04 | 1.51 | 11.14 |
| 20 | 0 | 0.440 | 0.075 | 0.45 | 0.2342 | 0.0399 | 14.72 | 2.51 | 14.93 |
| 25 | 0 | 0.510 | 0.090 | 0.52 | 0.2715 | 0.0479 | 17.06 | 3.01 | 17.32 |
| 30 | 0 | 0.630 | 0.090 | 0.64 | 0.3354 | 0.0479 | 21.07 | 3.01 | 21.29 |
| 35 | 0 | 0.740 | 0.075 | 0.74 | 0.3939 | 0.0399 | 24.75 | 2.51 | 24.88 |
| 40 | 0 | 0.840 | 0.060 | 0.84 | 0.4472 | 0.0319 | 28.10 | 2.01 | 28.17 |
| 45 | 0 | 0.940 | 0.080 | 0.94 | 0.5004 | 0.0426 | 31.44 | 2.68 | 31.56 |
| 50 | 0 | 1.020 | 0.060 | 1.02 | 0.5430 | 0.0319 | 34.12 | 2.01 | 34.18 |

TABLE 7

Legacy Lens 4: 8.75-Base Legacy Lens of Dual Lens System (Simulation)

| Viewing Axis Angle (degrees) | | Prismatic Power (diopters) | | | Angular Displacement (degrees) | | Apparent Displacement of Object at 100 Yards (inches) | | |
|---|---|---|---|---|---|---|---|---|---|
| Horizontal | Vertical | X | Y | R | $\theta_X$ | $\theta_Y$ | $D_X$ | $D_Y$ | $D_R$ |
| 0 | 0 | −0.030 | 0.030 | 0.04 | −0.0160 | 0.0160 | −1.00 | 1.00 | 1.42 |
| 5 | 0 | 0.090 | 0.000 | 0.09 | 0.0479 | 0.0000 | 3.01 | 0.00 | 3.01 |
| 10 | 0 | 0.210 | −0.015 | 0.21 | 0.1118 | −0.0080 | 7.02 | −0.50 | 7.04 |
| 15 | 0 | 0.280 | −0.020 | 0.28 | 0.1491 | −0.0106 | 9.37 | −0.67 | 9.39 |
| 20 | 0 | 0.480 | −0.030 | 0.48 | 0.2555 | −0.0160 | 16.06 | −1.00 | 16.09 |
| 25 | 0 | 0.550 | −0.030 | 0.55 | 0.2928 | −0.0160 | 18.40 | −1.00 | 18.42 |
| 30 | 0 | 0.730 | −0.050 | 0.73 | 0.3886 | −0.0266 | 24.42 | −1.67 | 24.47 |
| 35 | 0 | 0.800 | −0.070 | 0.80 | 0.4259 | −0.0373 | 26.76 | −2.34 | 26.86 |
| 40 | 0 | 0.980 | −0.090 | 0.98 | 0.5217 | −0.0479 | 32.78 | −3.01 | 32.92 |

TABLE 8

Redesigned Legacy Lens 4, Having a Freeform Rear Surface Resulting in a True Angle Optical Profile (Simulation)

| Viewing Axis Angle (degrees) | | Prismatic Power (diopters) | | | Angular Displacement (degrees) | | Apparent Displacement of Object at 100 Yards (inches) | | |
|---|---|---|---|---|---|---|---|---|---|
| Horizontal | Vertical | X | Y | R | $\theta_X$ | $\theta_Y$ | $D_X$ | $D_Y$ | $D_R$ |
| 0 | 0 | 0.040 | 0.000 | 0.04 | 0.0213 | 0.0000 | 1.34 | 0.00 | 1.34 |
| 5 | 0 | 0.060 | 0.000 | 0.06 | 0.0319 | 0.0000 | 2.01 | 0.00 | 2.01 |
| 10 | 0 | 0.070 | 0.020 | 0.07 | 0.0373 | 0.0106 | 2.34 | 0.67 | 2.44 |
| 15 | 0 | 0.080 | 0.020 | 0.08 | 0.0426 | 0.0106 | 2.68 | 0.67 | 2.76 |
| 20 | 0 | 0.100 | 0.020 | 0.10 | 0.0532 | 0.0106 | 3.34 | 0.67 | 3.41 |
| 25 | 0 | 0.120 | 0.025 | 0.12 | 0.0639 | 0.0133 | 4.01 | 0.84 | 4.10 |
| 30 | 0 | 0.140 | 0.025 | 0.14 | 0.0745 | 0.0133 | 4.68 | 0.84 | 4.76 |
| 35 | 0 | 0.160 | 0.030 | 0.16 | 0.0852 | 0.0160 | 5.35 | 1.00 | 5.45 |
| 40 | 0 | 0.170 | 0.040 | 0.17 | 0.0905 | 0.0213 | 5.69 | 1.34 | 5.84 |
| 45 | 0 | 0.190 | 0.040 | 0.19 | 0.1011 | 0.0213 | 6.36 | 1.34 | 6.49 |
| 50 | 0 | 0.200 | 0.050 | 0.21 | 0.1065 | 0.0266 | 6.69 | 1.67 | 6.90 |

TABLE 9

Vision Shield (Unitary & Freeform), Having Freeform Front & Rear Surfaces Resulting in a True Angle Optical Profile (Actual Measurement)

| Viewing Axis Angle (degrees) | | Prismatic Power (diopters) | | | Angular Displacement (degrees) | | Apparent Displacement of Object at 100 Yards (inches) | | |
|---|---|---|---|---|---|---|---|---|---|
| Horizontal | Vertical | X | Y | R | $\theta_X$ | $\theta_Y$ | $D_X$ | $D_Y$ | $D_R$ |
| 0 | 0 | −0.120 | 0.090 | 0.15 | −0.0639 | 0.0479 | −4.01 | 3.01 | 5.02 |
| 5 | 0 | −0.105 | 0.090 | 0.14 | −0.0559 | 0.0479 | −3.51 | 3.01 | 4.63 |
| 10 | 0 | −0.090 | 0.090 | 0.13 | −0.0479 | 0.0479 | −3.01 | 3.01 | 4.26 |
| 15 | 0 | 0.000 | 0.075 | 0.08 | 0.0000 | 0.0399 | 0.00 | 2.51 | 2.51 |
| 20 | 0 | 0.090 | 0.090 | 0.13 | 0.0479 | 0.0479 | 3.01 | 3.01 | 4.26 |
| 25 | 0 | 0.110 | 0.090 | 0.14 | 0.0586 | 0.0479 | 3.68 | 3.01 | 4.75 |
| 30 | 0 | 0.110 | 0.100 | 0.15 | 0.0586 | 0.0532 | 3.68 | 3.34 | 4.97 |
| 35 | 0 | 0.125 | 0.105 | 0.16 | 0.0665 | 0.0559 | 4.18 | 3.51 | 5.46 |
| 40 | 0 | 0.140 | 0.110 | 0.18 | 0.0745 | 0.0586 | 4.68 | 3.68 | 5.96 |
| 45 | 0 | 0.140 | 0.110 | 0.18 | 0.0745 | 0.0586 | 4.68 | 3.68 | 5.96 |
| 50 | 0 | 0.140 | 0.110 | 0.18 | 0.0745 | 0.0586 | 4.68 | 3.68 | 5.96 |
| 55 | 0 | 0.170 | 0.113 | 0.20 | 0.0905 | 0.0599 | 5.69 | 3.76 | 6.82 |
| 60 | 0 | 0.200 | 0.115 | 0.23 | 0.1065 | 0.0612 | 6.69 | 3.85 | 7.72 |
| 65 | 0 | 0.210 | 0.118 | 0.24 | 0.1118 | 0.0626 | 7.02 | 3.93 | 8.05 |
| 70 | 0 | 0.220 | 0.120 | 0.25 | 0.1171 | 0.0639 | 7.36 | 4.01 | 8.38 |
| 75 | 0 | 0.220 | 0.118 | 0.25 | 0.1171 | 0.0626 | 7.36 | 3.93 | 8.34 |
| 80 | 0 | 0.220 | 0.115 | 0.25 | 0.1171 | 0.0612 | 7.36 | 3.85 | 8.30 |
| 85 | 0 | 0.220 | 0.113 | 0.25 | 0.1171 | 0.0599 | 7.36 | 3.76 | 8.27 |
| 90 | 0 | 0.220 | 0.110 | 0.25 | 0.1171 | 0.0586 | 7.36 | 3.68 | 8.23 |

Exemplary Method for Designing a Freeform Lens for Eyewear to Produce a True Angle Optical Effect Method steps shall be described referencing corresponding flow diagrams. It is to be appreciated that not all steps in a flow diagram may be needed to perform the methods provided herein. Further, some of the steps may be performed simultaneously, or in a different order than shown in a flow diagram.

Figure 3:
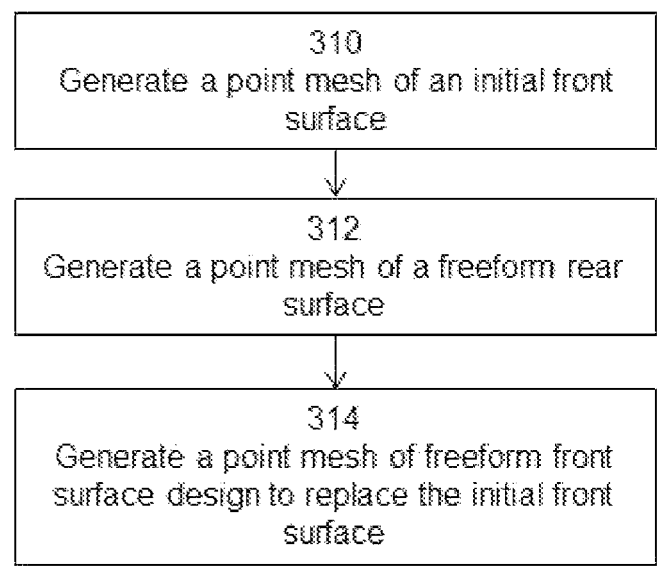
FIG. 3 is a flow diagram of general procedures for designing a lens with a freeform surface for eyewear, according to an example embodiment.

FIG. 3 illustrates general procedures for designing a freeform lens for eyewear to produce a true angle optical effect (also referred to herein as a "true angle optics method"), according to an exemplary embodiment. In an embodiment, at step 310, an initial front surface design is generated. The initial front surface may be configured to conform to a support structure (e.g., eyewear frame or protective headgear). The initial front surface may comprise a turned surface design and/or a freeform design lacking sufficient prismatic power reduction. In an embodiment, the initial front surface design is provided as a point mesh or 3D equation from which a point mesh may be derived (e.g., points that are solutions to the 3D equation). It is to be appreciated that the point mesh may be configured to have a pitch (center-to-center distance between points) so the resultant lens appears smooth and continuous to the wearer. In an embodiment, the point mesh is configured to have a pitch undiscernible by a typical user's eye, for example, smaller than approximately 10 μm. It is to be appreciated that the initial front surface may comprise a turned surface or other existing solutions that may or may not result in sufficient prismatic power reduction of the optic, initially. At step 312, a freeform rear surface design of the lens for eyewear is generated based on calculations of light refractions in consideration of the initial front surface design, to produce a true angle optical effect from the perspective of a wearer of the optic. At optional step 314, a freeform front surface design for the lens for eyewear is generated based on calculations of light refractions in consideration of the rear surface design. This freeform front surface may replace the initial front surface to provide an even more precise distortion correction.

Figure 4:
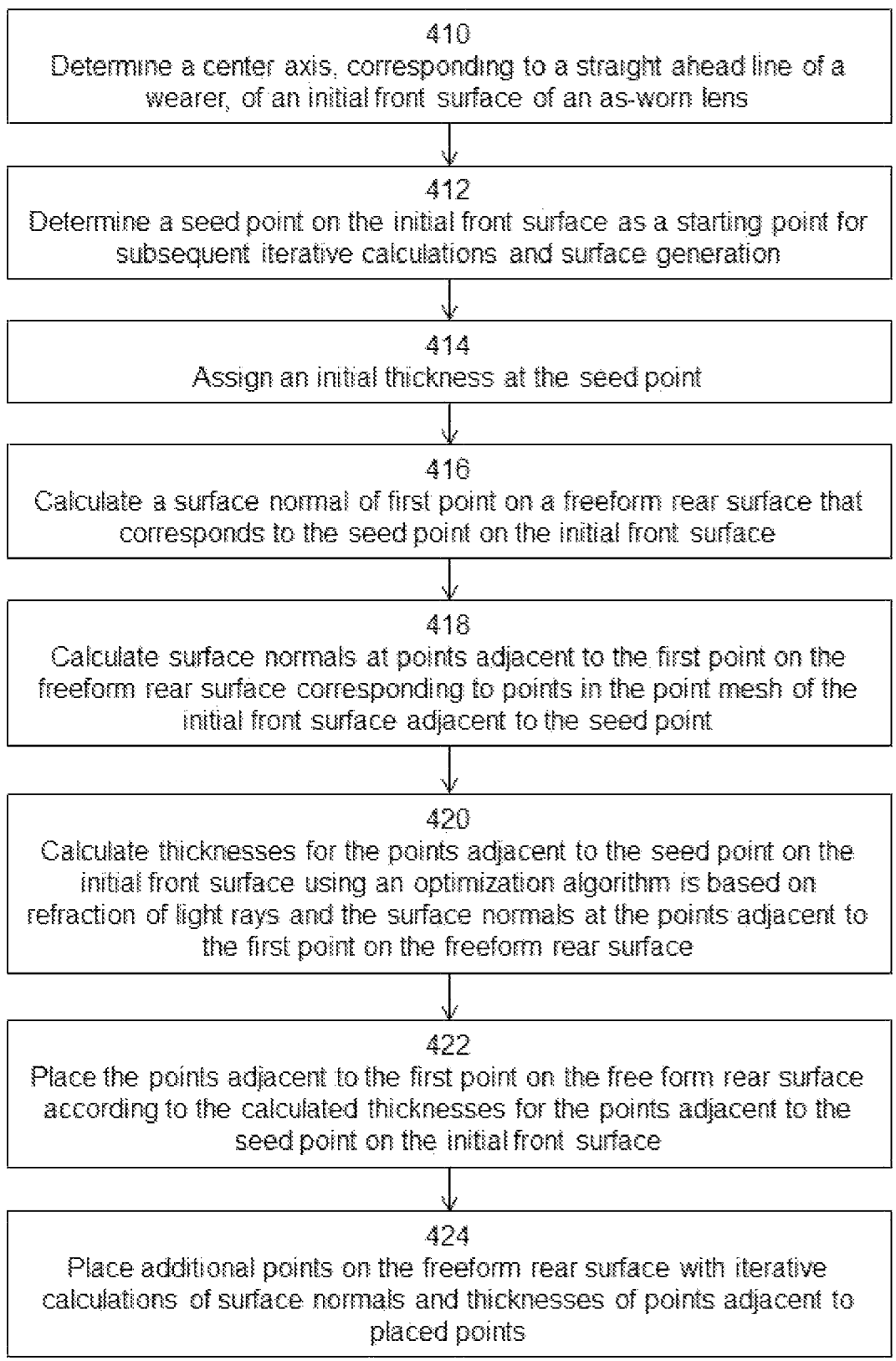
FIG. 4 is a flow diagram for generating a freeform rear surface design for a lens for eyewear, according to an example embodiment.

FIG. 4 illustrates procedures for generating a freeform rear surface design for an lens for eyewear that results in a true angle optical effect from the perspective of a wearer, according to an exemplary embodiment. It is to be appreciated that step 312 (FIG. 3) may comprise the procedures described herein in reference to FIG. 4. In an embodiment, at step 410, a center axis corresponding to a straight ahead line of sight of a wearer is determined for an initial front surface, for example, the initial front surface determined in step 310 (FIG. 3). The straight ahead line of sight axis may depend on an expected position of the optic relative to a user's eyes and an expected viewing posture of the user. It is to be appreciated that the expected position of the optic relative to a typical wearer's eyes and the expected viewing posture may vary depending on type of eyewear and activities of the wearer (e.g., unitary sunglasses or a visor mounted on a football helmet, motorcycle helmet, aircraft pilot helmet, heads-up for biking, or heads-down for golfing or fishing) and that these may be derived from actual measurements performed on test subjects or computer simulations.

At step 412, portions of the initial front surface are determined for optimization according to various optical solutions. In an embodiment, optical solutions may comprise a center axis (also called "all vectors forward") viewing solution, an off-axis viewing solution, and a solution outside a field-of-view (FOV). It is to be appreciated that off-axis viewing comprises viewing directions that are substantially different from the forward viewing direction, e.g., viewing through a lateral side of a visor. In an embodiment, the initial front surface is divided into a center portion, a transition portion, and a lateral portion. The transition portion connects the center portion and the lateral portion. In an embodiment, the center portion is associated with the forward viewing solution, the lateral portion is associated with the off-axis viewing solution, and the transition portion provides smooth and gradual transition between the forward viewing solution and the off-axis viewing solution. In an embodiment, the forward viewing solution may comprise binocular vision considerations and the off-axis solution may comprise single-eye (monocular) vision considerations. In an embodiment, the transitional boundary between binocular and monocular solutions may be placed where off-axis viewing angles become large enough to place one eye's line of sight such that it is occluded by a typical wearer's nose (i.e., the wearer's view becomes monocular at this boundary). One of skill in the art will recognize that although the description herein refers to a "lateral" portion or direction, embodiments of the invention are equally applicable to improving distortion in any off-axis direction, such as a vertical off-axis direction or other non-forward/non-straight-ahead line of sight viewing directions (e.g., any combination of horizontal and vertical viewing angles at non-zero degrees with respect to a straight ahead line of sight—that is, any combination of horizontal and vertical image displacements).

At step 414, a seed point on the initial front surface is determined. In an embodiment, the seed point is to be a starting reference point for generating points on a freeform rear surface. In an embodiment, an initial thickness is assigned to the seed point. In an embodiment, the seed point is chosen from a point mesh of an initial front surface design (e.g., step 310 of FIG. 3). In an embodiment, the seed point lies on a symmetry plane denoting a horizontal symmetry of the optic. In an embodiment, the seed point lies on a line denoting the boundary of the center portion and the transition portion or the boundary of the transition portion and the lateral portion. In an embodiment, the seed point lies where a straight-ahead line of sight of a typical wearer penetrates the initial front surface. In an embodiment, the seed point is not chosen from a point mesh, and/or may be a point between mesh points.

At step 416, a surface normal is calculated at the seed point and a first freeform rear surface point is placed at the initial thickness on a line coinciding with the surface normal at the seed point. It is to be appreciated that every point on the initial front surface is associated with corresponding points on the freeform rear surface and that points on the freeform rear surface, other than the first rear surface point, have yet to be assigned surface normals and thicknesses. At step 418, surface normals are calculated for points adjacent to the first rear surface point. For an "all vectors forward" solution, it is to be appreciated that light rays parallel to the wearer's forward line of sight entering the front surface are generally refracted within the lens thickness into directions not parallel to the forward line of sight, and that the rear surface normal for each ray is calculated such that the rays are returned to parallel with the forward line of sight upon exiting the lens rear surface. Furthermore, it is to be appreciated that for an "off axis" solution, light rays directed toward the wearer's eye entering the front surface are generally refracted within the lens thickness into directions not directed toward the wearers eye, and that the rear surface normal for each ray is calculated such that the rays are re-directed toward the wearer's eye upon exiting the lens rear surface. A person of skill in the art will recognize that the path of a transmitted light ray through the lens depends on the thickness of the lens at that point and the index of refraction of the particular lens material(s) in use, such that the thickness and the material's index of refraction is considered in the surface normal calculations. For example, lenses made of polycarbonate typically have a refractive index of 1.58+/−0.015. As discussed below, other materials and blends may be used for the lens, such that different refractive indexes would be used in the calculations. At step 420, an optimization algorithm assigns thicknesses to the points adjacent to the first rear surface point and places them at the thickness assigned to the at least one adjacent point. In an embodiment, the optimization algorithm follows a priority order comprising a most uniform optical path length solution, a thinnest possible solution, and a most uniform thickness solution such that the optimization algorithm outputs surface normals that are substantially similar to those calculated in step 418.

In an embodiment, the lens may also be designed to conform to other structures, for example, face contours such as the nose and/or cheeks. The conformance of the lens to another structure may involve an inflection point, for example, a concave to convex transition along a surface of a lens (e.g., surface 508 and/or 510, FIG. 5; surface 612 and/or 614, FIG. 6). The phrase "surface of the lens" refers to a surface extending from one portion of a perimeter of the lens to another portion of the perimeter of the lens. The term "inflection" may be used herein in the context of surfaces having smooth variations (e.g., no abrupt changes or interruptions on the surface). An example of an abruptly changing surface may be a cut or hole through a thickness of a lens body which can produce a surface that has a sharp 90 degree turn (e.g., a key hole). Another example of an abruptly changing surface may be a sharply angled, non-filleted protrusion of the lens (e.g., a hook for engaging with a frame).

Figure 14:
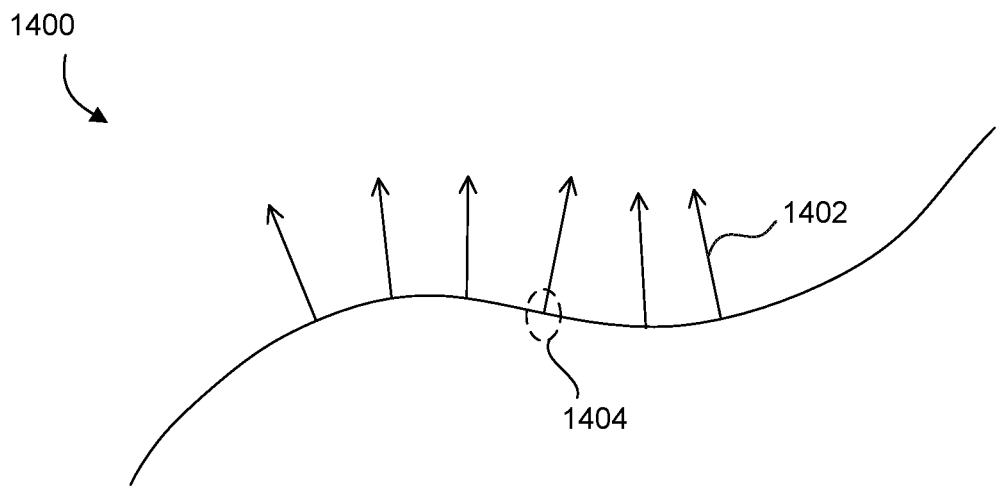
FIG. 14 is a cross section schematic illustration of a curved surface, according to an example embodiment.

FIG. 14 is a cross section illustration of a structure 1400 having a curved surface, according to an exemplary embodiment. In an embodiments, the curved surface of structure 1400 has surface normals 1402 (90 degrees with respect to surface) with orientations that depend on the curvature of the surface. Inflection point 1404 indicates where the curved surface switches from convex to concave and vice versa. Some of surface normals 1402 are shown to diverge, which indicate a convex surface. Some of surface normal are shown to converge, which shows a concave surface. A lens, having a two-dimensional surface, may comprise more than one inflection point. Therefore, in an embodiment, an inflection region may comprise a distribution of inflection points distributed on a line or throughout an area on a surface of a lens (e.g., on surface 612 and/or 614, FIG. 6).

In an embodiment, an inflection region may occur in any portion of a lens (e.g., center portion, lateral portion, and/or transition portion). That is, inflection regions may occur at surface areas having an all vectors forward solution and/or an off-axis solution. Designing inflection regions in portions having an all vectors forward solution may comprise true angle optical calculations to create a corresponding secondary surface (e.g., a secondary surface is designed based on an initial surface or another calculated surface). The secondary surface may be designed to deliver to a typical wearer the same optical effect that would have been produced if the inflection region were not present. In an embodiment, the inflection region's optical calculations may intentionally create the same off-angle distortions that the typical wearer would perceive if the inflection zone was absent, particularly when the inflection region lies in a portion of the lens intended to have an all vectors forward solution and is located on a portion of the lens where the user's gaze is directed slightly away from the forward direction (e.g., 5° off-axis). In other words, the optical behavior of a real and present inflection region would be as though the inflection region were absent. Described differently, even if the calculations are capable of drastically reducing prismatic distortions altogether at the inflection region, the lens is allowed to maintain some intentional distortion. That is, the calculations at the inflection region may be performed to match the prismatic power of the inflection region to the prismatic power just outside of (or adjacent to) the inflection region (e.g., no abrupt change in prismatic power), so that any resultant distortion substantially matches what would be perceived with a lens without the inflection region.

Abrupt changes in prismatic power can be more easily perceived by a user of the lens. An advantage of minimizing abrupt changes in prismatic power is that the user does not perceive a sudden distortion discontinuity as their gaze sweeps from one region of the lens to another.

In an embodiment, an inflection region may occur in a lateral portion of the lens. Designing inflection regions in portions having an off-axis solution may comprise true angle optical calculations to create a corresponding secondary surface. The secondary surface may be designed to continue the off-axis solution into, across, and beyond the inflection area. In an embodiment, rather than preserving prismatic distortions as described previously for the all vectors forward scenario, inflection regions with the off-axis solution continue to minimize the prismatic distortion. A reason for doing so is because inflection regions with an off-axis solution would nominally not include distortions up to, across, or beyond the inflection regions.

In an embodiment, an inflection region may occur in a transition portion of the lens. Designing inflection regions in portions having both an all vectors forward and an off-axis solution may comprise true angle optical calculations to create a corresponding secondary surface. The inflection region may comprise a gradient between a preservation of prismatic distortion to a minimization of prismatic distortion corresponding to a solution gradient between the center portion and the lateral portion.

In an embodiment, inflection regions may not conform to any of all vectors forward or off-axis solutions, for example, in areas of the lens where light ray incidence angles are large enough to create a total internal reflection situation (e.g., steep contoured surfaces conforming to the sides of a typical wearer's nose). Nevertheless, the method steps described above may allow all or a portion of an inflection region to deliver an intended optical effect to the user of the lens, to an extent not otherwise achievable through conventional lens designs.

Though embodiments of the present disclosure provide methods to design a lens by using an initial front surface point mesh as a basis to generate a freeform rear surface, one of skill in the art will recognize that a variation of the method is possible where an initial rear surface point mesh is used as a basis to generate a freeform front surface. It is to be appreciated that a particular solution in the priority order may be given a higher or lower priority or omitted. The embodiments described herein are exemplary and not limiting.

One of skill in the art will recognize that a lens design may be realized in a number of fabrication methods known in the art. For example, high optical quality lenses may be cut from a preformed injection molded lens blank. Alternatively, the lens may be molded directly into its final shape and size, to eliminate the need for post molding cutting steps. The lens, or the lens blank from which it is cut, may be injection molded and may comprise a relatively rigid and optically acceptable material, such as polycarbonate. Any material suitable for use as lenses may be employed, such as polymer, polycarbonate (or PC), allyl diglycol carbonate monomer (being sold under the brand name CR-39®), glass (e.g., crown glass, flint glass), nylon, polyurethane, polyethylene, polyimide, polyethylene terephthalate (or PET), biaxially-oriented polyethylene terephthalate polyester film (or BoPET, with one such polyester film sold under the brand name MYLAR®), acrylic (e.g., polymethyl methacrylate or PMMA), urethane-based pre-polymer and high-index hybrids (e.g., Trivex®, Tribrid™), high-index plastics, transparent high-index monomers, transparent high-index polymers, a polymeric material, a co-polymer, a doped material, any other suitable material, or any combination of materials. The geometry of surfaces of the lens may be created in the lens blank molding and polishing processes, and the lens shape may be cut from the blank. The fabrication methods described above are exemplary and not limiting.

Exemplary Lens for Eyewear

A lens for use in eyewear is typically required to comply with safety standards set by market demands or by a regulatory body, for example, a sport organization. While the below description is made primarily in the context of non-corrective eyewear, a person skilled in the art will recognize that similar techniques may be used to improve corrective eyewear as well. Typically, material and thickness are two interrelated safety parameters of lenses for eyewear, for example, a material with high shatter resistance may allow for a thinner lens geometry than another material with a lower shatter resistance. The refractive behavior of lens for eyewear is impacted by choices of materials and thicknesses, which in turn affect the magnitude of prismatic distortion, especially at off-axis viewing directions (e.g., lateral viewing directions and other non-forward viewing directions). A forward viewing direction of a lens for eyewear typically suffers little to no prismatic distortion for a wide range of materials and thicknesses because most conventional lenses are developed for forward viewing angles and, therefore, light rays from a forward viewing direction emerge after passing through the lens with directions and positions substantially similar to light rays in the absence of the lens. However, light rays directed at a wearer's eye and incident on an off-axis viewing area of the lens have larger angles of incidence, which causes light to refract and substantially deviate from a path corresponding to an absence of the lens. Though designing a thinner lens is a potential solution to this problem, the ability to design a thinner lens to reduce prismatic power may be limited by safety standards. Further, a thinner lens may become more flexible and lose optical benefits as the lens bends. The present disclosure provides a lens for eyewear that allows for reduction of prismatic power at off-axis viewing directions while maintaining thicknesses that meet a variety of regulatory safety standards.

Figure 5:
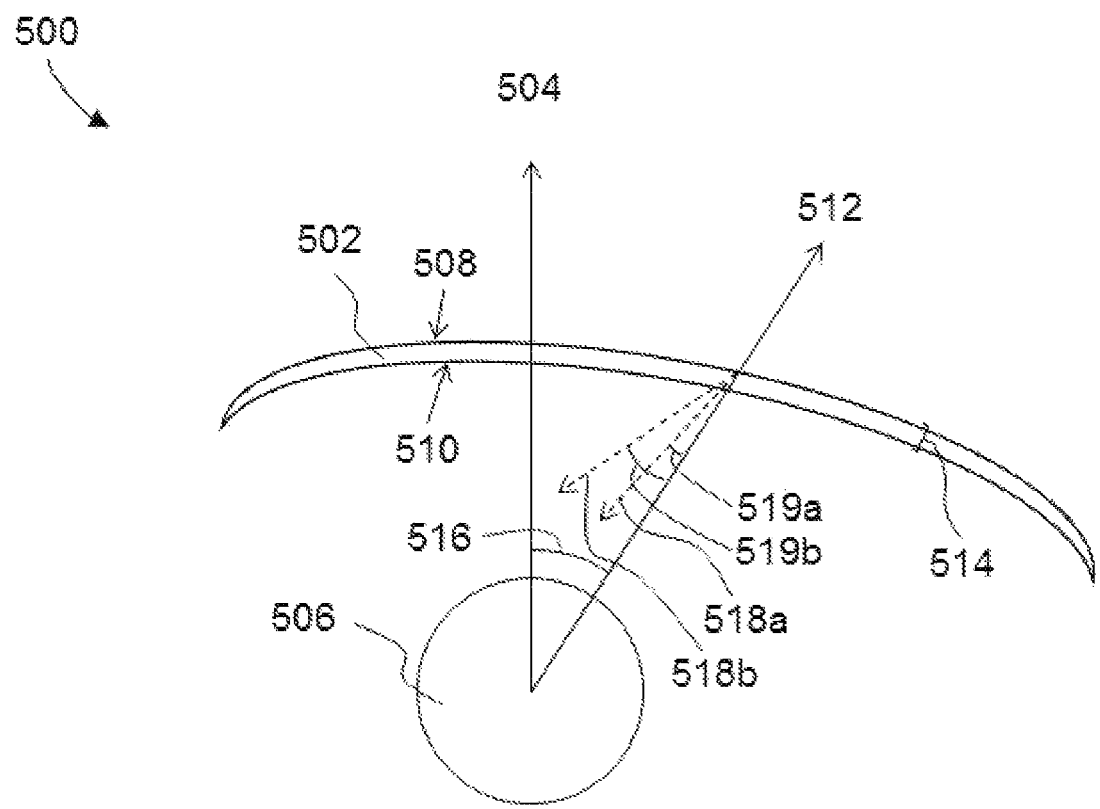
FIG. 5 is a top-view schematic illustration of a lens for dual lens eyewear, according to an example embodiment.

FIG. 5 is a schematic illustration of a lens 500 for use in dual lens eyewear, according to an exemplary embodiment. In an embodiment, lens 500 comprises a lens body 502 and is configured to be positioned in the path of a straight ahead line of sight that forms central axis 504 of one eye 506 of a typical wearer. It is to be appreciated that lens body 500 may be designed to be made of lens material commonly used in the art and that the lens material is chosen, based on intended application, for their optical and mechanical properties, for example, low/high refractive indices (e.g., 1.4-1.8), dispersion properties, UV attenuation, and impact resistance properties, among others. The materials may include polycarbonate, CR-39, Trivex, Tribrid, glass, and PMMA, among others. In an embodiment, lens body 502 comprises a front surface 508 and a rear surface 510. In an embodiment, a lens thickness 514 is defined between front surface 508 and rear surface 510. In an embodiment, lens thickness 514 at any point on the lens body is no greater than 4 mm and no less than 1 mm. In an embodiment, lens thickness 514 at any point on the lens body is no greater than 4 mm and no less than 2 mm. In an embodiment, lens thickness 514 at any point on the lens body is no greater than 3.5 mm and no less than 2 mm. In an embodiment, lens thickness 514 at any point on the lens body is no greater than 3.5 mm and no less than 2.5 mm. In an embodiment, lens thickness 514 at any point on the lens body is no greater than 3 mm and no less than 2 mm. In an embodiment, lens thickness 514 at any point on the lens body is no greater than 2 mm and no less than 1 mm. In an embodiment, lens thickness 514 at any point on the lens body is no greater than 1.7 mm and no less than 1.2 mm. One of skill in the art will recognize that other minimum and maximum thicknesses of lens thickness 514 may also be used as well.

Figure 12:
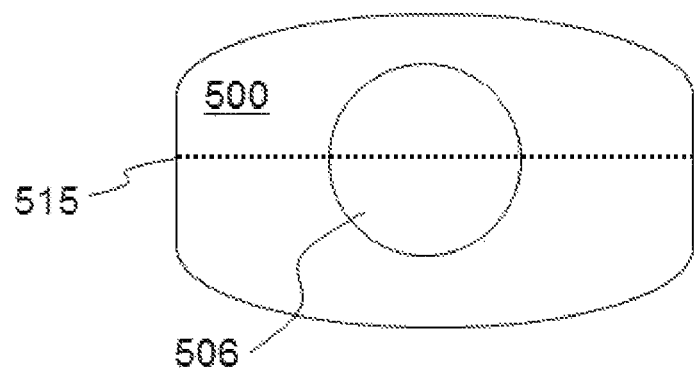
FIG. 12 is a plan-view schematic illustration of a lens for dual lens eyewear, according to an example embodiment.

In an embodiment, a viewing axis 512 extends from eye 506 and from center axis 504 at an angle 516 away from the typical wearer's nose that is measured along (e.g., follows along) a horizontal meridian 515 (see FIG. 12) of rear surface 510. In an embodiment, each point along the horizontal meridian is associated with an angle of viewing axis 512 where viewing axis 512 intersects the each point along horizontal meridian 515.

In an embodiment, front surface 508 has a turned surface (e.g., spheric, toric, or cylindrical geometry) and rear surface 510 has a freeform geometry. In an embodiment, front surface 508 has a freeform geometry and rear surface 510 has a turned surface. In an embodiment, both front surface 508 and rear surface 510 have freeform geometries. Since lenses for eyewear may have a number of different base curves, embodiments described herein account for different base curves of a lens. In an embodiment, a surface having spheric, toric, or cylindrical geometries may have a horizontal base curve of approximately base 4 or greater. In an embodiment, a surface having spheric, toric, or cylindrical geometries may have a horizontal base curve of approximately base 6 or greater. In an embodiment, a surface having spheric, toric, or cylindrical geometries may have a horizontal base curve of approximately base 8 or greater. In an embodiment, a surface having spheric, toric, or cylindrical geometries may have a horizontal base curve of approximately base 8.75 or greater. In an embodiment, a surface having spheric, toric, or cylindrical geometries may have a horizontal base curve of approximately base 10 or greater. A person of skill in the art will recognize that embodiments of the invention may be applied to lenses having any non-zero base curve in the horizontal and/or vertical directions. A person of skill in the art will further recognize that for turned surfaces having a given base curve, the lens blank base curve may not sit on exact horizontal or vertical lines as mounted in the eyewear or headgear. It is to be appreciated that freeform surfaces, though lacking a clearly defined single-valued base curve, may have an average surface curvature comparable to a specific turned surface so as to provide wraparound characteristics similar to turned surfaces.

As discussed above, lens 500 may be designed having turned surfaces as front surface 508 and rear surface 510. Without the correction provided for by embodiments of the present disclosure, prismatic power of lens 500 may cause a light ray 518 incoming from along viewing axis 512 to deviate from viewing axis 512 after passing through lens 500, which may cause prismatic distortion (e.g., an apparent shift of a location of an object at a distance). FIG. 5 shows different deviation amounts of light ray 518, which is indicated by angular amounts 519 and depends on lens parameters, e.g., lens thickness 514 or lens material, among other parameters. For example, one deviation amount is illustrated by light ray 518a and corresponding angle 519a, and a further deviation amount is illustrated by light ray 518b and corresponding angle 519b. Embodiments described herein, however, use freeform geometry on front surface 508 and/or rear surface 510 to reduce the prismatic power of lens 500 (e.g., reduce deviation amount of light ray 518). It is shown in Tables 1-9 that lenses employing embodiments of the present disclosure may achieve lower prismatic power than legacy lenses.

In an embodiment, a prismatic power of lens 500, employing a freeform geometry on front surface 508 and/or rear surface 510, does not exceed approximately 0.25 diopter throughout points along horizontal meridian 515 associated with angles of viewing axis 512 approximately 30 degrees or less. In an embodiment, a prismatic power of lens 500, employing a freeform geometry on front surface 508 and/or rear surface 510, does not exceed approximately 0.35 diopter throughout points along horizontal meridian 515 associated with angles of viewing axis 512 approximately 40 degrees or less. In an embodiment, a prismatic power of lens 500, employing a freeform geometry on front surface 508 and/or rear surface 510, does not exceed approximately 0.6 diopter throughout points along horizontal meridian 515 associated with angles of viewing axis 512 approximately 55 degrees or less. In an embodiment, a prismatic power of lens 500, employing a freeform geometry on front surface 508 and/or rear surface 510, does not exceed approximately 0.8 diopter throughout points along horizontal meridian 515 associated with angles of viewing axis 512 approximately 80 degrees or less.

In an embodiment, a prismatic power of lens 500, employing a freeform geometry on front surface 508 and/or rear surface 510, increases at an average rate not exceeding approximately 0.01 diopter per degree of increasing angle of viewing axis 512 throughout points along horizontal meridian 515 associated with angles of viewing axis 512 approximately 30 degrees or less. In an embodiment, a prismatic power of lens 500, employing a freeform geometry on front surface 508 and/or rear surface 510, increases at an average rate not exceeding approximately 0.01 diopter per degree of increasing angle of viewing axis 512 throughout points along horizontal meridian 515 associated with angles of viewing axis 512 from approximately 30 degrees to approximately 40 degrees. In an embodiment, a prismatic power of lens 500, employing a freeform geometry on front surface 508 and/or rear surface 510, increases at an average rate not exceeding approximately 0.01 diopter per degree of increasing angle of viewing axis 512 throughout points along horizontal meridian 515 associated with angles of viewing axis 512 from approximately 40 degrees to approximately 55 degrees. In an embodiment, a prismatic power of lens 500, employing a freeform geometry on front surface 508 and/or rear surface 510, increases at an average rate not exceeding approximately 0.01 diopter per degree of increasing angle of viewing axis 512 throughout points along horizontal meridian 515 associated with angles of viewing axis 512 from approximately 55 degrees to approximately 80 degrees.

In an embodiment, a prismatic power, P, of lens 500, employing a freeform geometry on front surface 508 and/or rear surface 510, throughout points along the horizontal meridian 515 associated with angles, θ, of viewing axis 512 from approximately 30 degrees to approximately 55 degrees satisfies the relation $P \lesssim 0.01\theta - 0.07$. In an embodiment, a prismatic power, P, of lens 500, employing a freeform geometry on front surface 508 and/or rear surface 510, throughout points along horizontal meridian 515 associated with angles, θ, of viewing axis 512 from approximately 55 degrees to approximately 90 degrees satisfies the relation $P \lesssim 0.01\theta - 0.07$.

As demonstrated by the data shown in Tables 1-9 and FIGS. 7-10, embodiments of the present disclosure are capable of further improving optical performance of lens 500. Therefore, in an embodiment, a prismatic power of lens 500, employing a freeform geometry on front surface 508 and/or rear surface 510, increases at an average rate not exceeding approximately 0.009 diopter per degree of increasing angle of viewing axis 512. In an embodiment, a prismatic power of lens 500, employing a freeform geometry on front surface 508 and/or rear surface 510, increases at an average rate not exceeding approximately 0.008 diopter per degree of increasing angle of viewing axis 512.

As suggested in the above embodiments, designing lenses with calculated freeform surfaces allows a prismatic power of a lens to increase at a slower rate per degree of increasing angle of a viewing axis with respect to a straight ahead line of sight. As a result, in an embodiment, a difference between a maximum and minimum prismatic power of a lens, throughout a given range of viewing angles, may be smaller when compared to a legacy lens having substantially similar parameters (except that the legacy lens would not have a calculated free form surface).

Referring back to Tables 1-9, as an example, Legacy Lens 1 is shown to have a minimum prismatic power of 0.04 diopters (at 0 degrees horizontal) and a maximum prismatic power of 0.25 diopters (at 30 degrees horizontal) when considering only the horizontal viewing range of 0-30 degrees. In other words, Legacy Lens 1 has a prismatic power that varies by as much as 0.21 diopter (i.e., 0.25-0.04) in the horizontal viewing range of 0-30 degrees. However, Redesigned Legacy Lens 1 (having a calculated freeform surface) is shown to have a minimum prismatic power of 0.02 diopters (at 0 degrees horizontal) and a maximum prismatic power of 0.14 diopters (at 30 degrees horizontal) when considering only the horizontal viewing range of 0-30 degrees. In other words, Redesigned Legacy Lens 1 has a prismatic power that varies by as much as 0.12 diopter in the horizontal viewing range of 0-30 degrees. Therefore, Redesigned Legacy Lens 1 presents a considerable improvement compared to its non-freeform counterpart. Embodiments of the present disclosure are capable of deterring a total rise of prismatic power in a given range of viewing angles.

In an embodiment, a difference between a maximum and a minimum prismatic power of lens 500, employing a freeform geometry on front surface 508 and/or rear surface 510, does not exceed approximately 0.20, 0.19, 0.15, 0.12, 0.08, or 0.04 diopter throughout a range of points along horizontal meridian 515 associated with angles of viewing axis 512 approximately 30 degrees or less. In an embodiment, a difference between a maximum and a minimum prismatic power of lens 500, employing a freeform geometry on front surface 508 and/or rear surface 510, does not exceed approximately 0.32, 0.31, 0.25, 0.20, 0.15, or 0.10 diopter throughout a range of points along horizontal meridian 515 associated with angles of viewing axis 512 approximately 40 degrees or less. In an embodiment, a difference between a maximum and a minimum prismatic power of lens 500, employing a freeform geometry on front surface 508 and/or rear surface 510, does not exceed approximately 0.56, 0.55, 0.45, 0.35, 0.25, 0.15, or 0.05 diopter throughout a range of points along horizontal meridian 515 associated with angles of viewing axis 512 approximately 55 degrees or less.

Until now, the prismatic power of lens 500 has been discussed in general for all base curves. However, Tables 1-9 and FIGS. 7-10 indicate that lenses without a calculated freeform surface have diminishing optical performance as base curve values increase, e.g., the prismatic power of a legacy lens having a 6-base curve is poorer (higher value) to that of a legacy lens having a 4-base curve. Therefore, the prismatic power of lenses employing an embodiment of the present disclosure and having a specific base curve may be lower than those discussed in general for all base curves.

Base 6 Examples: In an embodiment, a prismatic power of lens 500, employing a freeform geometry on front surface 508 and/or rear surface 510 having a horizontal base curve of approximately base 6 or greater, does not exceed approximately 0.44 diopter throughout points along horizontal meridian 515 associated with angles of viewing axis 512 approximately 30 degrees or less. In an embodiment, a prismatic power of lens 500, employing a freeform geometry on front surface 508 and/or rear surface 510 having a horizontal base curve of approximately base 6 or greater, does not exceed approximately 0.64 diopter throughout points along horizontal meridian 515 associated with angles of viewing axis 512 approximately 40 degrees or less. In an embodiment, a prismatic power of lens 500, employing a freeform geometry on front surface 508 and/or rear surface 510 having a horizontal base curve of approximately base 6 or greater, does not exceed approximately 0.89 diopter throughout points along horizontal meridian 515 associated with angles of viewing axis 512 approximately 50 degrees or less. In an embodiment, a prismatic power of lens 500, employing a freeform geometry on front surface 508 and/or rear surface 510 having a horizontal base curve of approximately base 6 or greater, does not exceed approximately 1.33 diopter throughout points along horizontal meridian 515 associated with angles of viewing axis 512 approximately 80 degrees or less.

In an embodiment, a prismatic power of lens 500, employing a freeform geometry on front surface 508 and/or rear surface 510 having a horizontal base curve of approximately base 6 or greater, increases at an average rate not exceeding approximately 0.018 diopter per degree of increasing angle of viewing axis 512 throughout points along horizontal meridian 515 associated with angles of viewing axis 512 approximately 30 degrees or less. In an embodiment, a prismatic power of lens 500, employing a freeform geometry on front surface 508 and/or rear surface 510 having a horizontal base curve of approximately base 6 or greater, increases at an average rate not exceeding approximately 0.018 diopter per degree of increasing angle of viewing axis 512 throughout points along horizontal meridian 515 associated with angles of viewing axis 512 from approximately 30 degrees to approximately 40 degrees. In an embodiment, a prismatic power of lens 500, employing a freeform geometry on front surface 508 and/or rear surface 510 having a horizontal base curve of approximately base 6 or greater, increases at an average rate not exceeding approximately 0.018 diopter per degree of increasing angle of viewing axis 512 throughout points along horizontal meridian 515 associated with angles of viewing axis 512 from approximately 40 degrees to approximately 50 degrees. In an embodiment, a prismatic power of lens 500, employing a freeform geometry on front surface 508 and/or rear surface 510 having a horizontal base curve of approximately base 6 or greater, increases at an average rate not exceeding approximately 0.018 diopter per degree of increasing angle of viewing axis 512 throughout points along horizontal meridian 515 associated with angles of viewing axis 512 from approximately 50 degrees to approximately 80 degrees.

In an embodiment, a prismatic power, P, of lens 500, employing a freeform geometry on front surface 508 and/or rear surface 510 having a horizontal base curve of approximately base 6 or greater, throughout points along horizontal meridian 515 associated with angles, θ, of viewing axis 512 from approximately 30 degrees to approximately 50 degrees satisfies the relation $P \lesssim 0.018\theta - 0.1$. In an embodiment, a prismatic power, P, of lens 500, employing a freeform geometry on front surface 508 and/or rear surface 510 having a horizontal base curve of approximately base 6 or greater, throughout points along horizontal meridian 515 associated with angles, θ, of viewing axis 512 from approximately 50 degrees to approximately 90 degrees satisfies the relation $P \lesssim 0.018\theta - 0.1$.

As demonstrated by the data shown in Tables 1-9 and FIGS. 7-10, embodiments of the present disclosure are capable of further improving optical performance of lens 500. In an embodiment, a prismatic power of lens 500, employing a freeform geometry on front surface 508 and/or rear surface 510 having a horizontal base curve of approximately base 6 or greater, increases at an average rate not exceeding approximately 0.016 diopter per degree of increasing angle of viewing axis 512. In an embodiment, a prismatic power of lens 500, employing a freeform geometry on front surface 508 and/or rear surface 510 having a horizontal base curve of approximately base 6 or greater, increases at an average rate not exceeding approximately 0.014 diopter per degree of increasing angle of viewing axis 512.

In an embodiment, a difference between a maximum and a minimum prismatic power of lens 500, employing a freeform geometry on front surface 508 and/or rear surface 510 having a horizontal base curve of approximately base 6 or greater, does not exceed approximately 0.44, 0.36, 0.28, 0.20, 0.12 or 0.04 diopter throughout a range of points along horizontal meridian 515 associated with angles of viewing axis 512 approximately 30 degrees or less. In an embodiment, a difference between a maximum and a minimum prismatic power of lens 500, employing a freeform geometry on front surface 508 and/or rear surface 510 having a horizontal base curve of approximately base 6 or greater, does not exceed approximately 0.64, 0.54, 0.44, 0.34, 0.24, 0.14, or 0.04 diopter throughout a range of points along horizontal meridian 515 associated with angles of viewing axis 512 approximately 40 degrees or less. In an embodiment, a difference between a maximum and a minimum prismatic power of lens 500, employing a freeform geometry on front surface 508 and/or rear surface 510 having a horizontal base curve of approximately base 6 or greater, does not exceed approximately 0.89, 0.70, 0.55, 0.40, 0.25, or 0.10 diopter throughout a range of points along horizontal meridian 515 associated with angles of viewing axis 512 approximately 50 degrees or less. For example, as shown in Table 4, a lens according to an example embodiment having a toric 4×6 geometry and a given freeform rear surface has a difference between a maximum and a minimum prismatic power that does not exceed approximately 0.19 throughout a range of points associated with angles between 0 and 20 degrees.

In an embodiment, a difference between a maximum and a minimum prismatic power of lens 500, employing a freeform geometry on front surface 508 and/or rear surface 510 having a horizontal base curve of approximately base 6 or greater, does not exceed approximately 0.35, 0.28, 0.20, 0.12 or 0.04 diopter throughout a range of points along horizontal meridian 515 associated with angles of viewing axis 512 from approximately 20 degrees to approximately 40 degrees. In an embodiment, a difference between a maximum and a minimum prismatic power of lens 500, employing a freeform geometry on front surface 508 and/or rear surface 510 having a horizontal base curve of approximately base 6 or greater, does not exceed approximately 0.43, 0.36, 0.28, 0.20, 0.12 or 0.04 diopter throughout a range of points along horizontal meridian 515 associated with angles of viewing axis 512 from approximately 30 degrees to approximately 50 degrees.

Embodiments using both a freeform surface and a turned surface along with other ranges of viewing angles and prismatic power performance are within the scope of the present disclosure. As a non-limiting example, in an embodiment, a difference between a maximum and a minimum prismatic power of lens 500, wherein front surface 508 has one of a toric or freeform geometry and rear surface 510 has the other of the toric and freeform geometry, does not exceed approximately 0.44, 0.40, 0.36, 0.32, 0.28, 0.24, 0.20, 0.16, 0.12, 0.08, or 0.04 diopter throughout a range of points along horizontal meridian 515 associated with angles of viewing axis 512 approximately 30 degrees or less. In an embodiment, a difference between a maximum and a minimum prismatic power of lens 500, wherein front surface 508 has one of a toric or freeform geometry and rear surface 510 has the other of the toric and freeform geometry, does not exceed approximately 0.35, 0.32, 0.29, 0.26, 0.23, 0.20, 0.17, 0.14, 0.11, 0.08, 0.05, or 0.02 diopter throughout a range of points along horizontal meridian 515 associated with angles of viewing axis 512 from approximately 20 degrees to approximately 40 degrees.

Base 8.75 Examples: As a further example of possible embodiments in reference to Tables 1-9 and FIGS. 7-10, non-limiting specific examples of a lens are provided in reference to Tables 6-8 and the graph of FIG. 9. In an embodiment, a prismatic power of lens 500, employing a freeform geometry on front surface 508 and/or rear surface 510 having a horizontal base curve of approximately base 8.75 or greater, does not exceed approximately 0.62 diopter throughout points along horizontal meridian 515 associated with angles of viewing axis 512 approximately 30 degrees or less. In an embodiment, a prismatic power of lens 500, employing a freeform geometry on front surface 508 and/or rear surface 510 having a horizontal base curve of approximately base 8.75 or greater, does not exceed approximately 0.82 diopter throughout points along horizontal meridian 515 associated with angles of viewing axis 512 approximately 40 degrees or less. In an embodiment, a prismatic power of lens 500, employing a freeform geometry on front surface 508 and/or rear surface 510 having a horizontal base curve of approximately base 8.75 or greater, does not exceed approximately 1.0 diopter throughout points along horizontal meridian 515 associated with angles of viewing axis 512 approximately 50 degrees or less. In an embodiment, a prismatic power of lens 500, employing a freeform geometry on front surface 508 and/or rear surface 510 having a horizontal base curve of approximately base 8.75 or greater, does not exceed approximately 1.56 diopter throughout points along horizontal meridian 515 associated with angles of viewing axis 512 approximately 80 degrees or less. For example, as shown in Table 8, a lens according to an example embodiment having a horizontal base curve of base 8.75 and a given freeform rear surface has a difference between a maximum and a minimum prismatic power that does not exceed approximately 0.08 throughout a range of points associated with angles between 0 and 25 degrees (wherein the difference is obtained by subtracting the prismatic power of 0.04 for an angle of 0 degrees from the prismatic power of 0.12 for an angle of 25 degrees).

In an embodiment, a difference between a maximum and a minimum prismatic power of lens 500, employing a freeform geometry on front surface 508 and/or rear surface 510 having a horizontal base curve of approximately base 8.75 or greater, does not exceed approximately 0.56, 0.44, 0.36, 0.28, 0.20, 0.12 or 0.04 diopter throughout a range of points along horizontal meridian 515 associated with angles of viewing axis 512 approximately 30 degrees or less. In an embodiment, a difference between a maximum and a minimum prismatic power of lens 500, employing a freeform geometry on front surface 508 and/or rear surface 510 having a horizontal base curve of approximately base 8.75 or greater, does not exceed approximately 0.78, 0.68, 0.54, 0.44, 0.34, 0.24, 0.14, or 0.04 diopter throughout a range of points along horizontal meridian 515 associated with angles of viewing axis 512 approximately 40 degrees or less. In an embodiment, a difference between a maximum and a minimum prismatic power of lens 500, employing a freeform geometry on front surface 508 and/or rear surface 510 having a horizontal base curve of approximately base 8.75 or greater, does not exceed approximately 0.94, 0.80, 0.75, 0.60, 0.45, 0.30, 0.18, or 0.05 diopter throughout a range of points along horizontal meridian 515 associated with angles of viewing axis 512 approximately 50 degrees or less. In another non-limiting specific embodiment of a lens based on Tables 6-8 and the graph of FIG. 10, a difference between a maximum and a minimum prismatic power of lens 500, employing a freeform geometry on front surface 508 and/or rear surface 510 having a horizontal base curve of approximately base 8.75 or greater, does not exceed approximately 0.39, 0.37, 0.35, 0.33, 0.31, 0.29, 0.27, 0.25, 0.23, 0.21, 0.19, 0.17, 0.15, 0.13, 0.11, 0.09, 0.07, 0.05, 0.03, or 0.01 diopter throughout a range of points along horizontal meridian 515 associated with angles of viewing axis 512 from approximately 20 degrees to approximately 40 degrees.

In an embodiment, a prismatic power of lens 500, employing a freeform geometry on front surface 508 and/or rear surface 510 having a horizontal base curve of approximately base 8.75 or greater, increases at an average rate not exceeding approximately 0.019 diopter per degree of increasing angle of viewing axis 512 throughout points along horizontal meridian 515 associated with angles of viewing axis 512 approximately 30 degrees or less. In an embodiment, a prismatic power of lens 500, employing a freeform geometry on front surface 508 and/or rear surface 510 having a horizontal base curve of approximately base 8.75 or greater, increases at an average rate not exceeding approximately 0.019 diopter per degree of increasing angle of viewing axis 512 throughout points along horizontal meridian 515 associated with angles of viewing axis 512 from approximately 30 degrees to approximately 40 degrees. In an embodiment, a prismatic power of lens 500, employing a freeform geometry on front surface 508 and/or rear surface 510 having a horizontal base curve of approximately base 8.75 or greater, increases at an average rate not exceeding approximately 0.019 diopter per degree of increasing angle of viewing axis 512 throughout points along horizontal meridian 515 associated with angles of viewing axis 512 from approximately 40 degrees to approximately 50 degrees. In an embodiment, a prismatic power of lens 500, employing a freeform geometry on front surface 508 and/or rear surface 510 having a horizontal base curve of approximately base 8.75 or greater, increases at an average rate not exceeding approximately 0.019 diopter per degree of increasing angle of viewing axis 512 throughout points along horizontal meridian 515 associated with angles of viewing axis 512 from approximately 50 degrees to approximately 80 degrees.

In an embodiment, a prismatic power, P, of lens 500, employing a freeform geometry on front surface 508 and/or rear surface 510 having a horizontal base curve of approximately base 8.75 or greater, throughout points along horizontal meridian 515 associated with angles, θ, of viewing axis 512 from approximately 30 degrees to approximately 50 degrees satisfies the relation $P \leq 0.019\theta + 0.04$. In an embodiment, a prismatic power, P, of lens 500, employing a freeform geometry on front surface 508 and/or rear surface 510 having a horizontal base curve of approximately base 8.75 or greater, throughout points along horizontal meridian 515 associated with angles, θ, of viewing axis 512 from approximately 50 degrees to approximately 90 degrees satisfies the relation $P \leq 0.019\theta + 0.04$.

As demonstrated by the data shown in Tables 1-9 and FIGS. 7-10, embodiments of the present disclosure are capable of further improving optical performance of lens 500. In an embodiment, a prismatic power of lens 500, employing a freeform geometry on front surface 508 and/or rear surface 510 having a horizontal base curve of approximately base 8.75 or greater, increases at an average rate not exceeding approximately 0.015 diopter per degree of increasing angle of viewing axis 512. In an embodiment, a prismatic power of lens 500, employing a freeform geometry on front surface 508 and/or rear surface 510 having a horizontal base curve of approximately base 8.75 or greater, increases at an average rate not exceeding approximately 0.011 diopter per degree of increasing angle of viewing axis 512. In an embodiment, a prismatic power of lens 500, employing a freeform geometry on front surface 508 and/or rear surface 510 having a horizontal base curve of approximately base 8.75 or greater, increases at an average rate not exceeding approximately 0.008 diopter per degree of increasing angle of viewing axis 512. In an embodiment, a prismatic power of lens 500, employing a freeform geometry on front surface 508 and/or rear surface 510 having a horizontal base curve of approximately base 8.75 or greater, increases at an average rate not exceeding approximately 0.004 diopter per degree of increasing angle of viewing axis 512.

Figure 6:
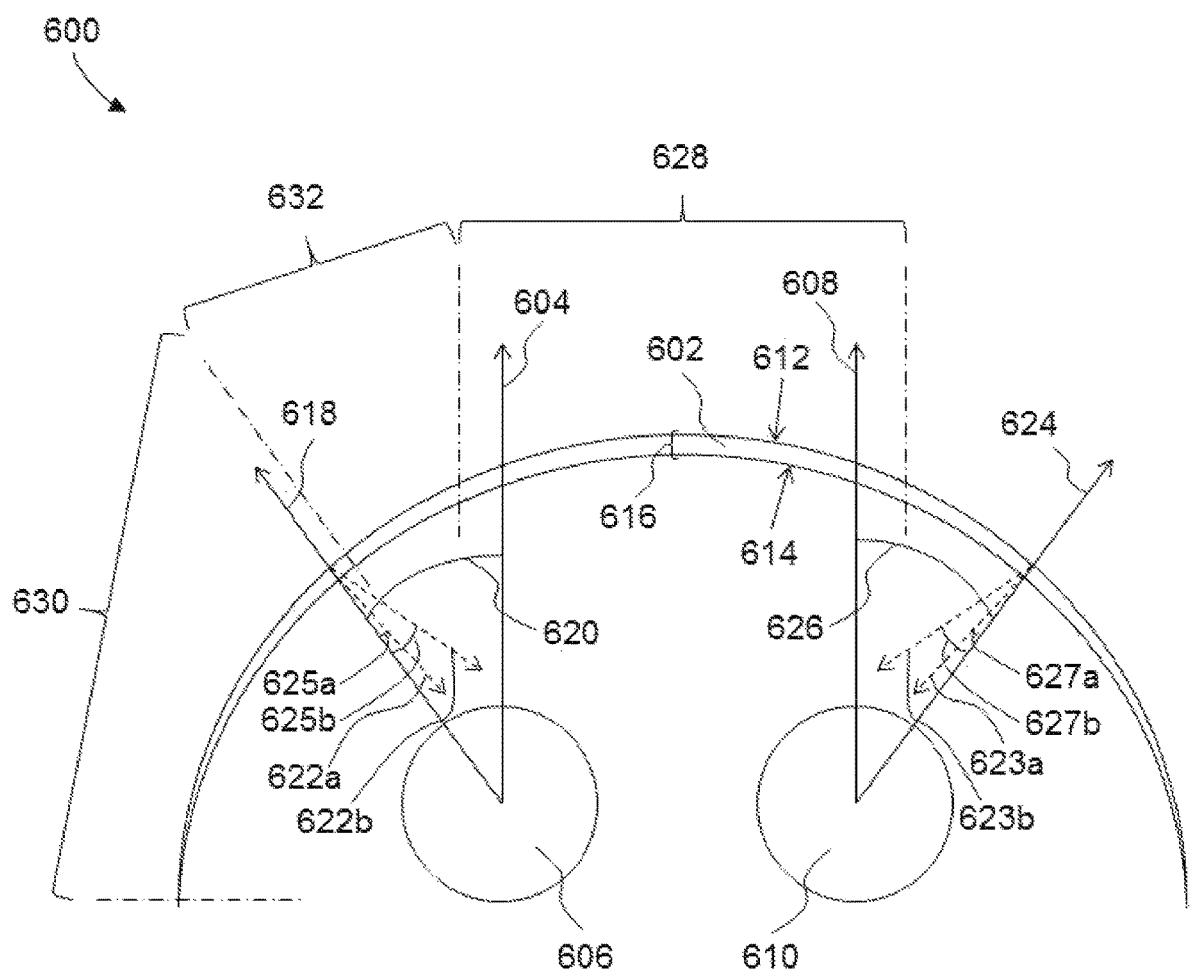
FIG. 6 is a top-view schematic illustration of a unitary lens for eyewear, according to an example embodiment.

FIG. 6 is a schematic illustration of a unitary lens 600 for use in non-corrective eyewear, according to an exemplary embodiment. In an embodiment, unitary lens 600 comprises a lens body 602 and is configured to be positioned in the path of a left center axis 604 corresponding to a straight ahead line of sight of a left eye 606 of a typical wearer and a right center axis 608 corresponding to a straight ahead line of sight of a right eye 610 of the average wearer. Materials considerations for lens body 602 are similar to those described previously for lens body 502 (FIG. 5). In an embodiment, lens body 602 comprises a front surface 612 and a rear surface 614. In an embodiment, a lens thickness 616 is defined between front surface 612 and rear surface 614. In an embodiment, lens thickness 616 at any point on lens body 602 is no greater than 2 mm and no less than 1 mm. In an embodiment, lens thickness 616 is no greater than 1.7 mm and no less than 1.2 mm. One of skill in the art will recognize that other minimum and maximum thicknesses of lens thickness 616 may also be used as well.

In an embodiment, a left viewing axis 618 extends from left eye 606 and from left center axis 604 at an angle 620 away from the typical wearer's nose that is measured along (e.g., follows along) a horizontal meridian 615 (FIG. 13) of rear surface 614. In an embodiment, each point of a set of points 617 (FIG. 13) along horizontal meridian 615 is associated with an angle of left viewing axis 618 where left viewing axis 618 intersects the each point of set of points 617.

In an embodiment, front surface 612 has a turned surface (e.g., spheric, toric, or cylindrical geometry) and rear surface 614 has a freeform geometry. In an embodiment, front surface 612 has a freeform geometry and rear surface 614 has a turned surface. In an embodiment, both front surface 612 and rear surface 614 have freeform geometries. Since lenses for eyewear may have a number of different base curves, embodiments described herein account for different base curves of a lens. In an embodiment, a surface having spheric, toric, or cylindrical geometries may have a horizontal base curve of approximately base 4 or greater. In an embodiment, a surface having spheric, toric, or cylindrical geometries may have a horizontal base curve of approximately base 6 or greater. In an embodiment, a surface having spheric, toric, or cylindrical geometries may have a horizontal base curve of approximately base 8 or greater. In an embodiment, a surface having spheric, toric, or cylindrical geometries may have a horizontal base curve of approximately base 10 or greater. It is to be appreciated that freeform surfaces, though lacking a single-valued base curve, may have an average surface curvature comparable to a specific turned surface so as to provide wraparound characteristics similar to turned surfaces.

Figure 11:
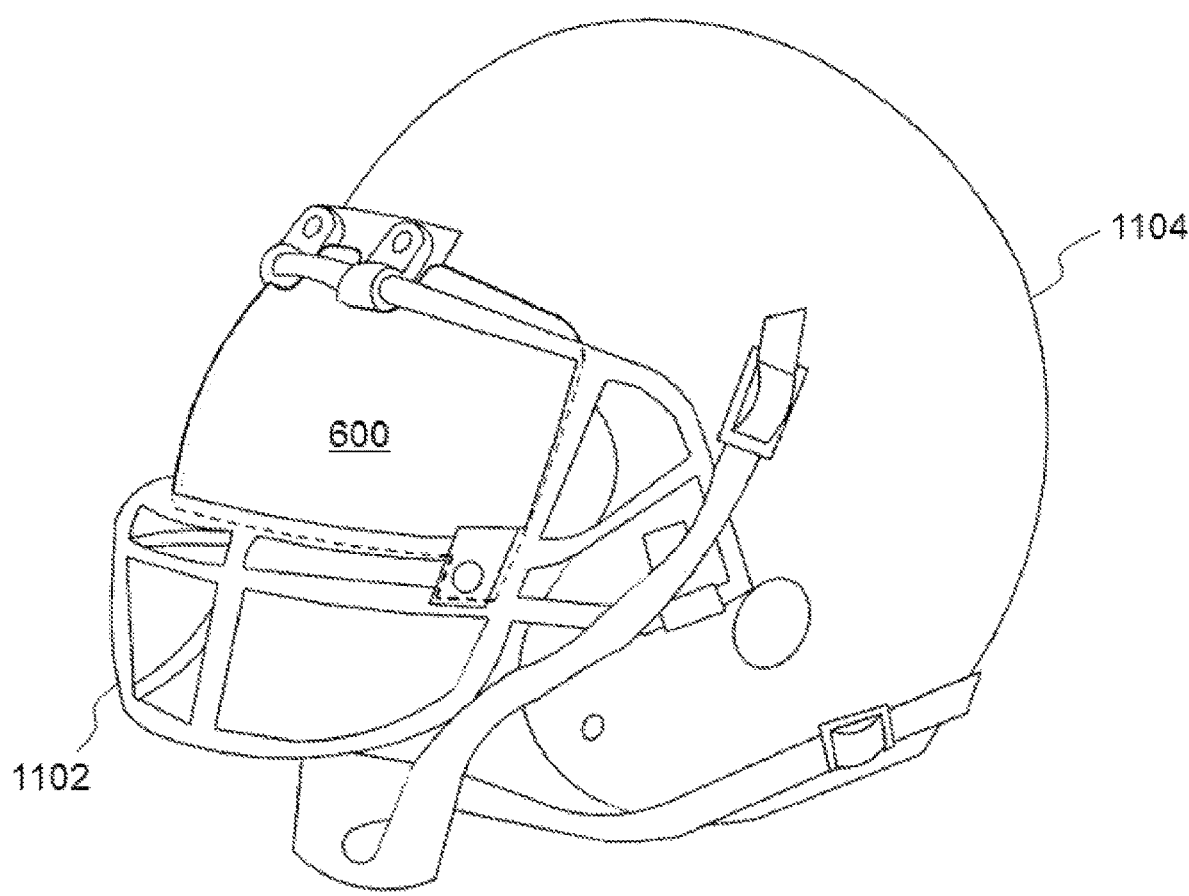
FIG. 11 is an illustration of an example lens attached to a protective headgear, according to an example embodiment.

In an embodiment, unitary lens 600 conforms to a frame and is configured to be affixed to the frame for supporting the lens on the wearer's head. In an embodiment, the frame comprises an eyeglass frame. The frame may include ear supports directly attached to the lens or ear supports attached to a face frame which supports unitary lens 600 (or lens 500 of FIG. 5) (e.g., rimless or rimmed eyeglasses, respectively). In an embodiment, the frame comprises a protective headgear 1104 (FIG. 11), e.g., a sport helmet, a motorcycle helmet, a construction hardhat, etc. In an embodiment, the frame comprises a goggle, e.g., a snow/ski goggle, a motorcycle goggle, among others. In such embodiments, the goggle may include a strap for supporting the goggle with the lens on the wearer's head. In an embodiment, unitary lens 600 conforms to an additional structure 1102 and is configured to be affixed on additional structure 1102 (FIG. 11) and additional structure 1102 is configured to be mounted to protective headgear 1104. Unitary lens 600 may also be designed to conform to other structures, for example, face contours such as the nose and/or cheeks. The conformance of unitary lens 600 to another structure may involve an inflection point, for example, a concave to convex transition. In the context of the present disclosure, an inflection region of unitary lens 600 may be an inflection line, as opposed to an inflection point (or a series of inflection points on a line).

In an embodiment, unitary lens 600 conforms to a user's facial contours, for example, the user's nose or cheeks. In an embodiment, unitary lens 600 comprises contours for moment of inertia management (e.g., features to increase or reduce stiffness of the lens), for aerodynamics management (e.g., features to increase, reduce, or redirect airflow for drag or defogging issues), and/or for aesthetic purposes. For conformations and contours, unitary lens 600 may comprise regions on front surface 612 and rear surface 614 having inflection regions, e.g., areas where the lens transitions between a generally convex shape to a generally concave shape, or vice versa.

As discussed above, unitary lens 600 may be designed having turned surfaces as front surface 612 and rear surface 614. Without the correction provided for by embodiments of the present disclosure, prismatic power of unitary lens 600 may cause a light ray 622 incoming from along left viewing axis 618 to deviate from left viewing axis 618 after passing through unitary lens 600, which may cause prismatic distortion (e.g., an apparent shift of a location of an object at a distance). A similar deviation may occur for a light ray 623 incoming from along right viewing axis 624 after passing through unitary lens 600. FIG. 6 shows different deviation amounts of light ray 622, which is indicated by angular amounts 625 and depend on lens parameters, e.g., lens thickness 616 or lens material, among other parameters. For example, one deviation amount is illustrated by light ray 622a and corresponding angle 625a, and a further deviation amount is illustrated by light ray 622b and corresponding angle 625b. Similarly for light ray 627, an example deviation amount is illustrated by light ray 623a and corresponding angle 627a, and another example deviation amount is illustrated by light ray 623b and corresponding angle 627b. Embodiments described herein, however, use freeform geometry on front surface 612 and/or rear surface 614 to reduce the prismatic power of unitary lens 600. It is shown in Tables 1-9 and FIGS. 7-10 that lenses employing embodiments of the present disclosure may achieve lower prismatic power than legacy lenses.

In an embodiment, a prismatic power of unitary lens 600, employing a freeform geometry on front surface 612 and/or rear surface 614, does not exceed approximately 0.25 diopter throughout points, of set of points 617, associated with angles of left viewing axis 618 approximately 30 degrees or less. In an embodiment, a prismatic power of unitary lens 600, employing a freeform geometry on front surface 612 and/or rear surface 614, does not exceed approximately 0.35 diopter throughout points, of set of points 617, associated with angles of left viewing axis 618 approximately 40 degrees or less. In an embodiment, a prismatic power of unitary lens 600, employing a freeform geometry on front surface 612 and/or rear surface 614, does not exceed approximately 0.6 diopter throughout points, of set of points 617, associated with angles of left viewing axis 618 approximately 55 degrees or less. In an embodiment, a prismatic power of unitary lens 600, employing a freeform geometry on front surface 612 and/or rear surface 614, does not exceed approximately 0.8 diopter throughout points, of set of points 617, associated with angles of left viewing axis 618 approximately 80 degrees or less.

In an embodiment, a prismatic power of unitary lens 600, employing a freeform geometry on front surface 612 and/or rear surface 614, increases at an average rate not exceeding approximately 0.01 diopter per degree of increasing angle of left viewing axis 618 throughout points, of set of points 617, associated with angles of left viewing axis 618 approximately 30 degrees or less. In an embodiment, a prismatic power of unitary lens 600, employing a freeform geometry on front surface 612 and/or rear surface 614, increases at an average rate not exceeding approximately 0.01 diopter per degree of increasing angle of left viewing axis 618 throughout points, of set of points 617, associated with angles of left viewing axis 618 from approximately 30 degrees to approximately 40 degrees. In an embodiment, a prismatic power of unitary lens 600, employing a freeform geometry on front surface 612 and/or rear surface 614, increases at an average rate not exceeding approximately 0.01 diopter per degree of increasing angle of left viewing axis 618 throughout points, of set of points 617, associated with angles of left viewing axis 618 from approximately 40 degrees to approximately 55 degrees. In an embodiment, a prismatic power of unitary lens 600, employing a freeform geometry on front surface 612 and/or rear surface 614, increases at an average rate not exceeding approximately 0.01 diopter per degree of increasing angle of left viewing axis 618 throughout points, of set of points 617, associated with angles of left viewing axis 618 approximately 80 degrees or less.

In an embodiment, a prismatic power, P, of unitary lens 600, employing a freeform geometry on front surface 612 and/or rear surface 614 throughout points, of set of points 617, associated with angles, θ, of left viewing axis 618 from approximately 30 degrees to approximately 55 degrees satisfies the relation $P \leq 0.01\theta - 0.07$. In an embodiment, a prismatic power, P, of unitary lens 600, employing a freeform geometry on front surface 612 and/or rear surface 614 throughout points, of set of points 617, associated with angles, θ, of left viewing axis 618 from approximately 55 degrees to approximately 90 degrees satisfies the relation $P \leq 0.01\theta - 0.07$.

Figure 13:
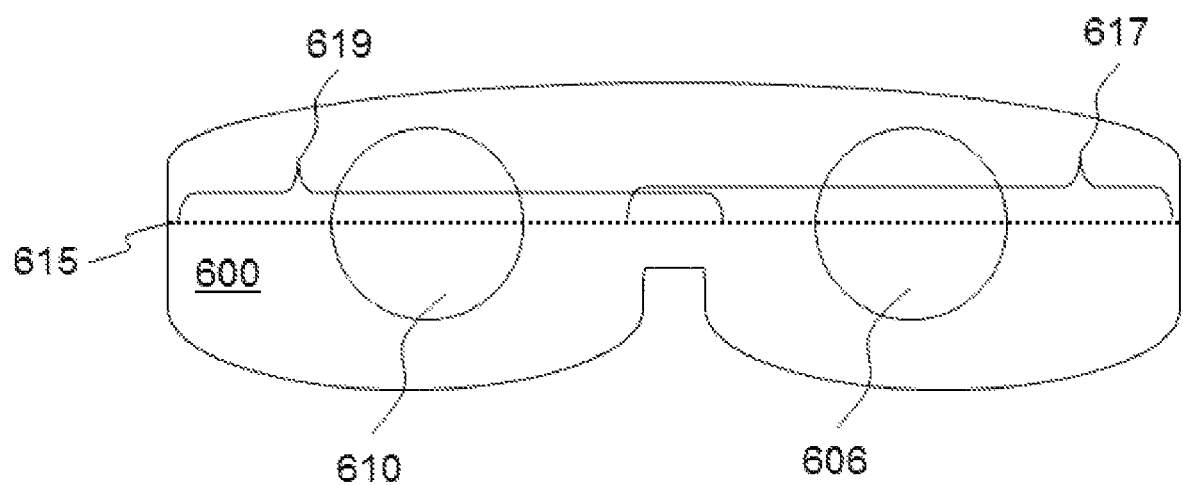
FIG. 13 is a plan-view schematic illustration of a unitary lens for eyewear, according to an example embodiment.

In an embodiment, a right viewing axis 624 extends from right eye 610 and from right center axis 608 at another angle 626 away from the typical wearer's nose that is measured along (e.g., follows along) horizontal meridian 615 (FIG. 13). In an embodiment, each point of a set of points 619 (FIG. 13) along horizontal meridian 615 is associated with an angle of right viewing axis 620 where right viewing axis 620 intersects the each point of the set of points 619. It is to be appreciated that prismatic power considerations regarding right eye 610 and right viewing axis 608 are similar, and may be mirrored, to the previously discussed prismatic power in embodiments regarding left viewing axis 604.

Furthermore, Tables 1-9 and FIGS. 7-10 show that embodiments of the present disclosure are capable of further improving optical performance of unitary lens 600, similar to previously discussed performance embodiments for lens 500 (FIG. 5) and that the prismatic power of lenses employing an embodiment of the present disclosure and having a specific base curve may be lower than those discussed in general for all base curves. Therefore, one skilled in the art will recognize that the prismatic power features previously discussed in embodiments of lens 500 may also be applied to unitary lens 600, and vice versa.

In an embodiment, unitary lens 600 comprises a center portion 628 and a lateral portion 630. In an embodiment, center portion 628 comprises a binocular forward viewing solution (e.g., all vectors forward viewing). In an embodiment, lateral portion 630 comprises a monocular off-axis viewing solution. In an embodiment, a transition portion 632 connects center portion 628 and lateral portion 630. In an embodiment, transition portion 632 provides a smooth and gradual transition between the binocular forward viewing solution of center portion 628 and the monocular off-axis viewing solution of lateral portion 630. In an embodiment, transition portion 632 is defined between angles of left viewing axis 618 from approximately 5 degrees to approximately 40 degrees. In an embodiment, transition portion 632 is defined between angles of left viewing axis 618 from approximately 10 degrees to approximately 30 degrees. In an embodiment, transition portion 632 is defined between angles of left viewing axis 618 from approximately 15 degrees to approximately 20 degrees. In an embodiment, transition portion 632 is defined between angles of left viewing axis 618 from approximately 5 degrees to approximately 15 degrees. In an embodiment, transition portion 632 is defined between angles of left viewing axis 618 from approximately 10 degrees to approximately 20 degrees. In an embodiment, transition portion 632 is defined between angles of left viewing axis 618 from approximately 15 degrees to approximately 25 degrees. In an embodiment, transition portion 632 is defined between angles of left viewing axis 618 from approximately 20 degrees to approximately 25 degrees. One of skill in the art will recognize that another lateral portion and another transition portion can be defined relative to angles of the right viewing axis 624 with similar limitations as those discussed above for transition portion 632.

Figure 15:
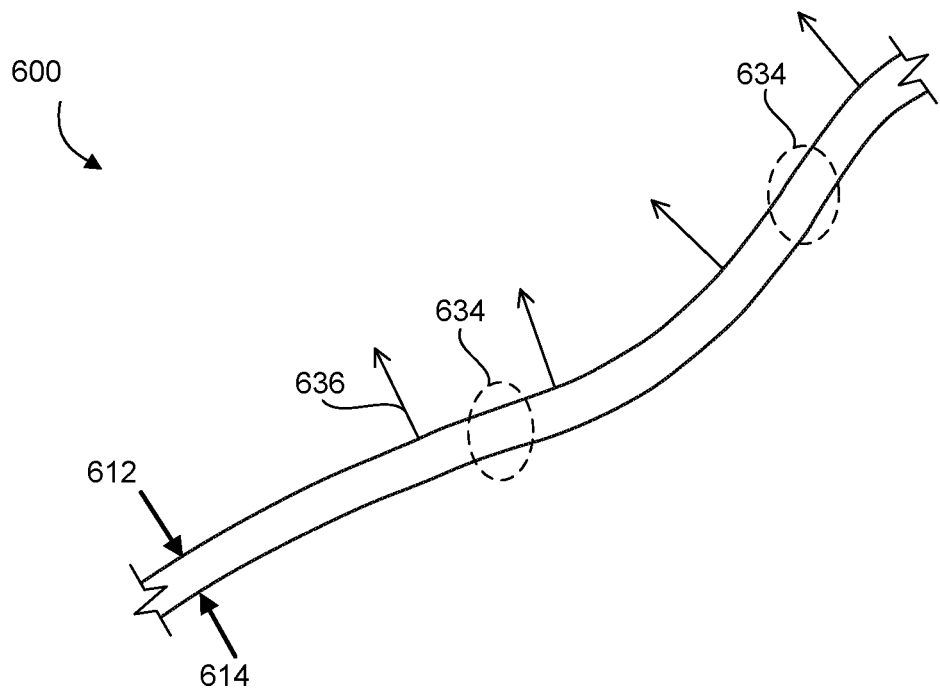
FIG. 15 is a top-view schematic illustration of a unitary lens, according to an example embodiment.

FIG. 15 is a schematic illustration of unitary lens 600, but of a different cross-section than the one shown in FIG. 6. The cross-section shown in FIG. 15 is one that would sit lower on a typical wearer's face (e.g., includes a contour of the nose). In an embodiment, unitary lens 600 comprises one or more inflection regions 634. One or more inflection regions 634 are designed to form contours in unitary lens 600 to, for example, conform to a typical wearer's facial features (e.g., nose bridge, cheeks, eye shallows). Surface normals 636 are drawn to indicate a concavity of the surface. Surface normals 636 diverge for a convex part of surface 612 and converge for a concave part of the surface 612. It should be appreciated that convex/concave behavior may be relative to which side of unitary lens 600 is referenced. For example, the convex part of surface 612 may be a concave part of surface 614. Though FIG. 15 uses unitary lens 600 as a reference, it should be appreciated that embodiments including inflections (e.g., inflection region 634) may be envisioned for any lens for eyewear (e.g., for lens 500 of FIG. 5). For example, the features related to inflection regions 634 for unitary lens 600 may be similarly applied to lens 500 (FIG. 5).

Referring back to FIG. 6, in an embodiment, inflection regions of unitary lens 600 may occur in any portion of unitary lens 600 (e.g., center portion 628, lateral portion 630, and/or transition portion 632). That is, inflection regions may occur in areas having an all vectors forward viewing solution and/or an off-axis viewing solution.

In an embodiment, unitary lens 600 comprises an inflection region disposed in center portion 628. The inflection region may be designed such that a prismatic distortion of the inflection region is matched to the prismatic distortion just outside of (or adjacent to) the inflection region.

In an embodiment, unitary lens 600 comprises an inflection region disposed in lateral portion 630. The inflection region may be designed such that a prismatic distortion of the inflection region is minimized.

In some embodiment, unitary lens 600 may be modified to achieve a dual lens solution, for example, by dividing (e.g., cutting or otherwise separating) unitary lens 600 in half such that a left eye lens and a right eye lens is produced. And, while some embodiment features have been discussed directly referencing a unitary lens or a lens for dual lens eyewear, it should be appreciated that any and all embodiment features described herein in reference to a unitary lens (e.g., unitary lens 600) may be applicable to a lens for dual lens eyewear (e.g., lens 500 of FIG. 5) and vice versa.

Though embodiments of the present disclosure concern lenses to be used in non-corrective eyewear, one of skill in the art will recognize that the peripheral viewing correction provided for by embodiments of the present disclosure may also be applied to prescription lenses having intentional (e.g., prescription) optical power and astigmatism.

Figure 7:
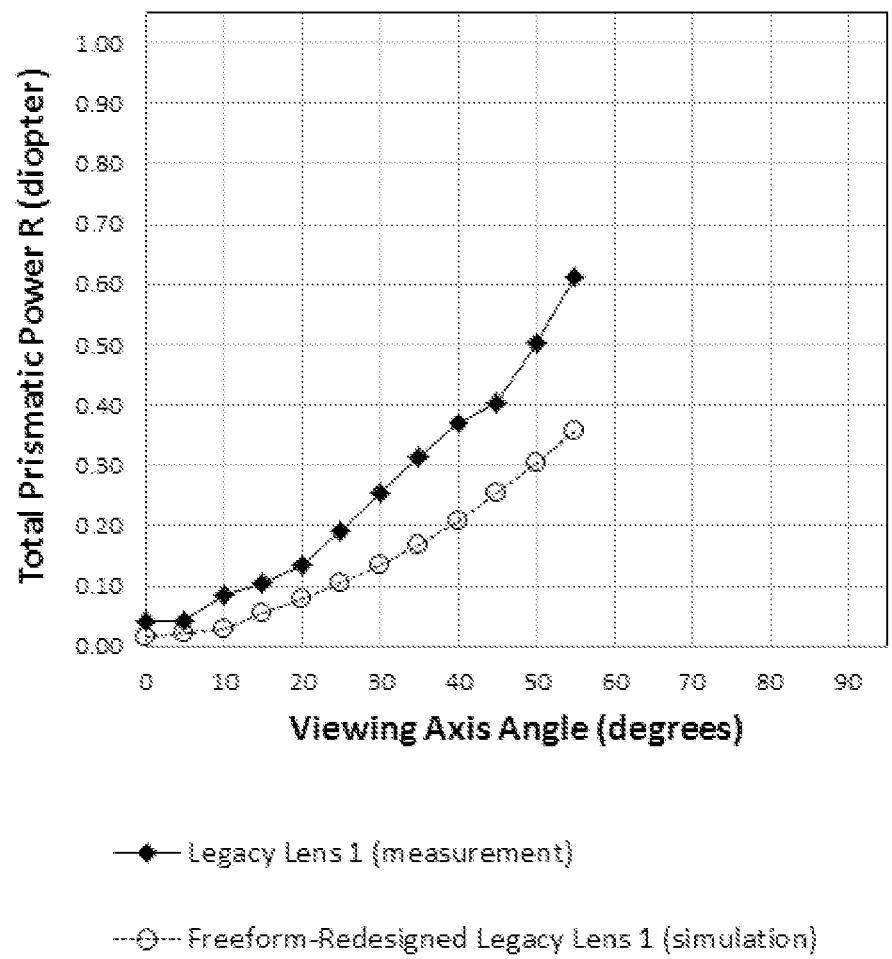
FIG. 7 is a graph plot of prismatic power data of a legacy lens and an example freeform-redesigned version of the legacy lens.

FIG. 7 is a graph plot comparing total prismatic power of original Legacy Lens 1 (measured) from Table 1 and the example freeform-redesigned Legacy Lens 1 (simulation) from Table 2. Values closer to 0 are preferred. The simulation shows an overall reduction of total prismatic power throughout the horizontal viewing axis angle range of Legacy Lens 1 when employing a freeform-redesign according to embodiments of the present disclosure.

Figure 8:
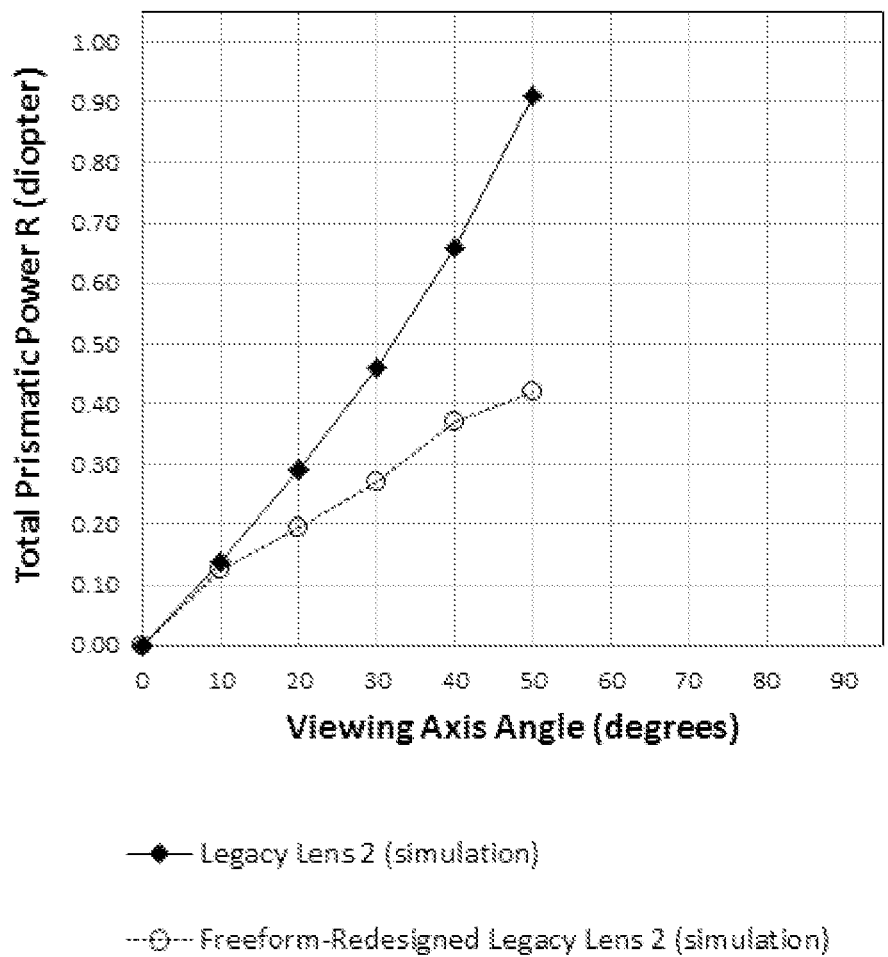
FIG. 8 is a graph plot of prismatic power data of a legacy lens and an example freeform-redesigned version of the legacy lens.

FIG. 8 is a graph plot comparing total prismatic power of original Legacy Lens 2 (simulation) from Table 3 and the example freeform-redesigned Legacy Lens 2 (simulation) from Table 4. Values closer to 0 are preferred. Similar to Legacy Lens 1 comparison, here, the simulation shows an overall reduction of total prismatic power throughout the horizontal viewing axis angle range of Legacy Lens 2 when employing a freeform-redesign according to embodiments of the present disclosure.

Figure 9:
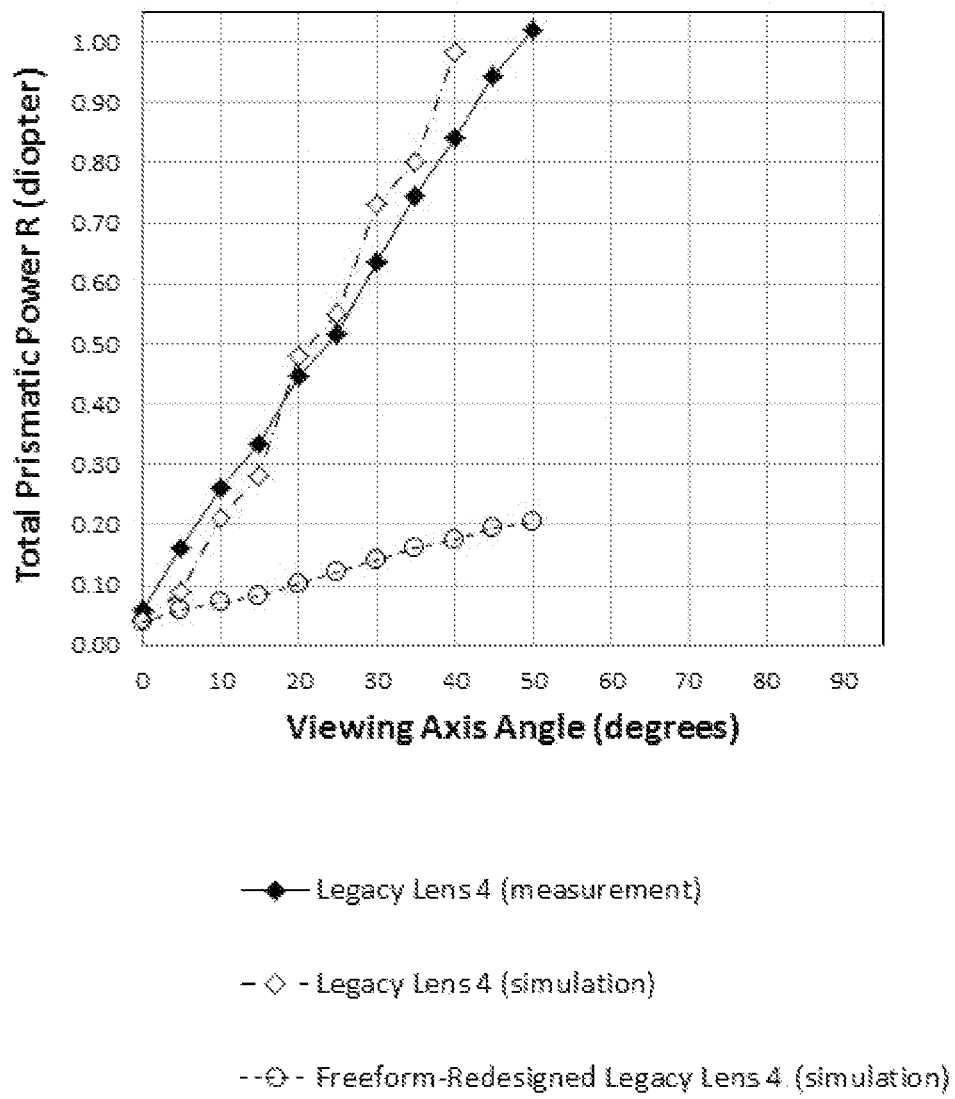
FIG. 9 is a graph plot of prismatic power data of a legacy lens and an example freeform-redesigned version of the legacy lens.

FIG. 9 is a graph plot comparing total prismatic power of original Legacy Lens 4 (measured) from Table 6, original Legacy Lens 4 (simulation) from Table 7, and the freeform-redesigned Legacy Lens 4 (simulation) from Table 8. Values closer to 0 are preferred. The simulation shows an overall reduction of total prismatic power throughout the horizontal viewing axis angle range of Legacy Lens 4 when employing a freeform-redesign according to embodiments of the present disclosure. The improvement of optical performance is more pronounced as compared to Legacy Lens 4, showing a reduction of prismatic power by approximately a factor of 5, than it is for Legacy Lens 1 or 2. Additionally, the fidelity of the simulation algorithm is corroborated here, where it is shown that simulated and measured prismatic power of Legacy Lens 4 are in good agreement.

Figure 10:
FIG. 10 is a graph plot of prismatic power data of a vision shield compared to a legacy lens.

FIG. 10 is a graph plot comparing a total prismatic power of the example freeform vision shield (measured) from Table 9 and original Legacy Lens 1 (measured) from Table 1. Values closer to 0 are preferred. This graph is that it compares actual measurements, the vision shield having a freeform-redesign according to embodiments in the present disclosure. The total prismatic power of the vision shield increases at a low rate, ranging 0.13-0.25 diopter between 20-90 degrees, and does not exceed 0.25 diopter throughout its horizontal viewing axis angle range.

Regarding metrics by which prismatic distortion is assessed, one of skill in the art will recognize that the prismatic powers referred to in embodiments of the present disclosure may be described in other equivalent terms. For example, a feature described in terms of prismatic power may also be described in terms of angular displacement or deflection, an apparent displacement of an object at a given distance from a wearer, or other equivalent metrics, some of which are demonstrated in Tables 1-9. The metrics used herein to assess prismatic distortion are exemplary and not limiting.

One of skill in the art will recognize that a lens surface may comprise geometry having a variable base curve. For example, the vision shield measurements shown in Table 9 and FIG. 10 has a variable base curve across the lens end-to-end, ranging between 3-10. The frontal viewing region, which may be defined from approximately 25 degrees to the left to 25 degrees to the right (e.g., as in viewing axis angles), has a base curve in the range 5.5-10, with base 10 being located more central.

It should be appreciated that embodiments including prismatic power performance may cover any range of viewing angles, and it should be understood that the present disclosure includes any and all ranges of view angles despite not providing an exhaustive lists of all possible range combinations. For example, an embodiment was mentioned in reference to FIG. 5 where a prismatic power of lens 500, employing a freeform geometry on front surface 508 and/or rear surface 510 having a horizontal base curve of approximately base 6 or greater, increases at an average rate not exceeding approximately 0.018 diopter per degree of increasing angle of viewing axis 512 throughout points along horizontal meridian 515 associated with angles of viewing axis 512 from approximately 30 degrees to approximately 40 degrees. Here, the 30-40 degree horizontal viewing range is given as an example. Embodiments can be envisioned which are directed at, for example, a narrow range of off-axis viewing angles that are closer to a straight ahead line of sight (e.g., the range 20-40 degrees in the horizontal), or a large range of viewing angles that cover a large part of off-axis viewing (e.g., 10-90 degrees in the horizontal). In such embodiments, the prismatic power performance for a given angle range may be derived from values in tables 1-9.

As an example of a different angle range, in an embodiment referencing FIG. 5 and the data in Table 6, a difference between a maximum and a minimum prismatic power of lens 500, employing a freeform geometry on front surface 508 and/or rear surface 510 having a horizontal base curve of approximately base 8.75 or greater, does not exceed approximately 0.40, 0.30, 0.20, 0.10 or 0.05 diopter throughout a range of points along horizontal meridian 515 associated with angles of viewing axis 512 from approximately 25 degrees to approximately 45 degrees. For this embodiment, Table 6 shows data for many horizontal viewing angles, such as 25 through 45 degrees horizontal for a legacy lens having a base curve of approximately 8.75. The diopter difference between a maximum and a minimum value, for this legacy lens and this range of viewing angles, is about 0.42 diopter. Therefore, using the diopter improvement methods disclosed herein, a redesigned base 8.75 lens may have any diopter difference, between a maximum and minimum value, less than 0.42 (e.g., 0.40) for the chosen range of viewing angles (in this case approximately 25-45 degrees). Other so derived embodiments covering other ranges of viewing angles and prismatic power performance are within the scope of the present disclosure. Using the diopter improvement methods disclosed herein, a redesigned lens may have any diopter maximums or diopter differences for a given range of viewing angles which is better than its corresponding legacy lens, e.g., by 10%, 20%, 30%, 40%, 50%, 60%, 70%, 80% or more, as evidenced by Tables 1-9. In other words, while specific combination of angle ranges and diopter maximums and differences between minimums and maximums, have been disclosed herein, other combinations of viewing angle ranges and prismatic power improvements over legacy lenses, evidenced by and directly derivable from Tables 1-9, are within the scope of the present disclosure.

Similarly, embodiments may be directed at a lens surface having a particular geometry. Though the following example embodiments are directed at toric geometries, it should be appreciated that similar embodiments may be envisioned with spheric or cylindrical geometries. In reference to FIG. 6, in an embodiment, front surface 612 has one of a toric and freeform geometry and rear surface 614 has the other of the toric and freeform geometry. In an instance of such embodiment, a prismatic power of unitary lens 600, does not exceed approximately 0.44 diopter throughout points, of set of points 617, associated with angles of left viewing axis 618 approximately 30 degrees or less. In another instance of such embodiment, a prismatic power of unitary lens 600 does not exceed approximately 0.64 diopter throughout points, of set of points 617, associated with angles of left viewing axis 618 approximately 40 degrees or less. In yet another instance of such embodiment, a prismatic power of unitary lens 600 does not exceed approximately 0.89 diopter throughout points, of set of points 617, associated with angles of left viewing axis 618 approximately 50 degrees or less. And as mentioned previously, embodiments using both a freeform surface and a turned surface along with other ranges of viewing angles and prismatic power performance are within the scope of the present disclosure.

Various embodiments thus provide a method of furnishing a lens having at least one freeform surface (also referred to herein as a "true angle optic") for the varying angle of incidence from the wearer's eye to the surface of a lens. By recognizing a novel relationship among the wearer's line of sight and the unique configurations of the inner and outer surfaces of the lens described herein, the present disclosure allows use of any of a variety of lens designs while minimizing prismatic distortion. For example, a designer may choose a desirable orientation and curvature for the lens, relative to a wearer's line of sight. The orientation and curvature may be chosen from a wide range of rake (i.e., vertical "tilt" of the lens), horizontal cant, base curve value and proximity to a wearer's face, including those parameters resulting in a high degree of wrap. The freeform geometry of lens surfaces may then be chosen, by the method of the present disclosure, such that the prismatic distortion is minimized. This improvement has many advantages over legacy lenses, such as the ability to expand a lens design envelope for different styles, fit different pupil distances of a wearer with minimal degradation of optics, and set lenses in a wider range of frames/headgear designs.

While the above disclosure describes measurements and corrections relative to a horizontal viewing axis, one of skill in the art will recognize that similar techniques may be used for measurements and corrections relative to a vertical viewing axis, or in a direction or field having both horizontal and vertical components.

Although embodiments of the present disclosure have been disclosed, it will be understood by those skilled in the art that the present disclosure extends beyond the specifically disclosed embodiments to other alternative embodiments and/or uses of the invention and obvious modifications and equivalents thereof. In addition, while several variations of the embodiments have been shown and described in detail, other modifications, which are within the scope of the present disclosure, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments may be combined with or substituted for one another in order to form varying modes of the disclosed inventions. Thus, it is intended that the scope of at least part of the present disclosure herein disclosed should not be limited by the particular disclosed embodiments described above.

What is claimed is:

1. A lens for use in non-corrective eyewear or headgear in combination with a frame to support the lens in a path of a straight ahead line of sight forming a center axis of one eye of a typical wearer, the lens comprising:
 a lens body comprising:
  a front surface having one of a toric and freeform geometry; and
  a rear surface having the other of the toric and freeform geometry, wherein
   a viewing axis extends from the one eye and the center axis at an angle from the center axis away from the typical wearer's nose measured along a horizontal meridian of the rear surface,
   each point along the horizontal meridian of the rear surface is associated with an angle of the viewing axis where the viewing axis intersects the each point along the horizontal meridian of the rear surface,
   a prismatic power of the lens does not exceed approximately 0.33 diopter for every point along the horizontal meridian of the rear surface at angles of the viewing axis from 0 degrees to approximately 30 degrees, and
   the prismatic power of the lens does not exceed approximately 0.89 diopter for every point along the horizontal meridian of the rear surface at angles of the viewing axis from greater than approximately 30 degrees to approximately 50 degrees.

2. The lens of claim 1, wherein the prismatic power of the lens does not exceed approximately 0.61 diopter for every point along the horizontal meridian of the rear surface at angles of the viewing axis from greater than approximately 30 degrees to approximately 40 degrees.

3. The lens of claim 1, wherein:
the front surface has the toric geometry, and
the front surface has a horizontal base curve of approximately base 6 or greater.

4. The lens of claim 1, wherein:
the lens is a unitary lens,
the viewing axis is a first viewing axis,
the one eye is a first eye,
the unitary lens is configured to be supported in a path of a straight ahead line of sight forming a center axis of a second eye of the typical wearer,
a second viewing axis extends from the second eye and the center axis of the second eye at an angle from the center axis of the second eye away from the typical wearer's nose in a direction opposite that of the first viewing axis measured along the horizontal meridian of the rear surface,
each point of a second set of points along the horizontal meridian of the rear surface is associated with an angle of the second viewing axis where the second viewing axis intersects the each point of the second set of points, and
the prismatic power of the lens does not exceed approximately 0.33 diopter for every point of the second set of points at angles of the second viewing axis along the horizontal meridian of the rear surface from 0 degrees to approximately 30 degrees.

5. The lens of claim 1, wherein:
the rear surface further comprises an inflection region, and
a prismatic power at the inflection region matches a prismatic power of a region of the rear surface next to the inflection region.

6. A lens for use in non-corrective eyewear or headgear in combination with a frame to support the lens in a path of a straight ahead line of sight forming a center axis of one eye of a typical wearer, the lens comprising:
a lens body comprising:
a front surface having one of a toric and freeform geometry; and
a rear surface having the other of the toric and freeform geometry, wherein
a viewing axis extends from the one eye and the center axis at an angle from the center axis away from the typical wearer's nose measured along a horizontal meridian of the rear surface,
each point along the horizontal meridian of the rear surface is associated with an angle of the viewing axis where the viewing axis intersects the each point along the horizontal meridian of the rear surface,
a prismatic power of the lens does not exceed approximately 0.33 diopter for every point along the horizontal meridian of the rear surface at angles of the viewing axis from 0 degrees to approximately 30 degrees, and
a difference between a maximum and minimum prismatic power of the lens for a range of points along the horizontal meridian of the rear surface at angles of the viewing axis from approximately 30 degrees to approximately 40 degrees does not exceed approximately 0.18 diopter.

7. The lens of claim 6, wherein:
the prismatic power of the lens does not exceed approximately 0.61 diopter for every point along the horizontal meridian of the rear surface at angles of the viewing axis from greater than approximately 30 degrees to approximately 40 degrees.

8. The lens of claim 6, wherein:
the front surface has the toric geometry, and
the front surface has a horizontal base curve of approximately base 6 or greater.

9. The lens of claim 6, wherein:
the lens is a unitary lens,
the viewing axis is a first viewing axis,
the one eye is a first eye,
the unitary lens is configured to be supported in a path of a straight ahead line of sight forming a center axis of a second eye of the typical wearer,
a second viewing axis extends from the second eye and the center axis of the second eye at an angle from the center axis of the second eye away from the typical wearer's nose in a direction opposite that of the first viewing axis measured along the horizontal meridian of the rear surface,
each point of a second set of points along the horizontal meridian of the rear surface is associated with an angle of the second viewing axis where the second viewing axis intersects the each point of the second set of points, and
the prismatic power of the lens does not exceed approximately 0.33 diopter for every point of the second set of points at angles of the second viewing axis along the horizontal meridian of the rear surface from 0 degrees to approximately 30 degrees.

10. The lens of claim 6, wherein:
the rear surface further comprises an inflection region, and
a prismatic power at the inflection region matches a prismatic power of a region of the rear surface next to the inflection region.

11. A lens for use in non-corrective eyewear or headgear in combination with a frame to support the lens in a path of a straight ahead line of sight forming a center axis of one eye of a typical wearer, the lens comprising:
a lens body comprising:
a front surface having one of a toric and freeform geometry; and
a rear surface having the other of the toric and freeform geometry, wherein
a viewing axis extends from the one eye and the center axis at an angle from the center axis away from the typical wearer's nose measured along a horizontal meridian of the rear surface,
each point along the horizontal meridian of the rear surface is associated with an angle of the viewing axis where the viewing axis intersects the each point along the horizontal meridian of the rear surface,
a prismatic power of the lens does not exceed approximately 0.33 diopter for every point along the horizontal meridian of the rear surface at angles of the viewing axis from 0 degrees to approximately 30 degrees, and
a difference between a maximum and minimum prismatic power of the lens for a range of points along the horizontal meridian of the rear surface at angles of the viewing axis from approximately 30 degrees to approximately 50 degrees does not exceed approximately 0.43.

12. The lens of claim 11, wherein:
the prismatic power of the lens does not exceed approximately 0.61 diopter for every point along the horizontal meridian of the rear surface at angles of the viewing axis from greater than approximately 30 degrees to approximately 40 degrees.

13. The lens of claim 11, wherein:
the front surface has the toric geometry, and
the front surface has a horizontal base curve of approximately base 6 or greater.

14. The lens of claim 11, wherein:
the rear surface further comprises an inflection region, and
a prismatic power at the inflection region matches a prismatic power of a region of the rear surface next to the inflection region.

15. A lens for use in non-corrective eyewear or headgear in combination with a frame to support the lens in a path of a straight ahead line of sight forming a center axis of one eye of a typical wearer, the lens comprising:
a lens body comprising:
a front surface; and
a rear surface having a freeform geometry and comprising an inflection region, the inflection region comprising a concave to convex transition of the rear surface, wherein
a lens thickness is defined between the front surface and the rear surface,
a viewing axis extends from the one eye and the center axis at an angle from the center axis away from the typical wearer's nose measured along a horizontal meridian of the rear surface,
each point along the horizontal meridian of the rear surface is associated with an angle of the viewing axis where the viewing axis intersects the each point along the horizontal meridian of the rear surface, and
a prismatic power at the inflection region matches a prismatic power of a region of the rear surface next to the inflection region.

16. The lens of claim 15, wherein:
the front surface has a turned surface-geometry, and
the front surface has a horizontal base curve of approximately base 6 or greater.

17. The lens of claim 15, wherein a prismatic power of the lens does not exceed approximately 0.23 diopter for every point along the horizontal meridian of the rear surface at angles of the viewing axis from 0 degrees to approximately 30 degrees.

18. The lens of claim 17, wherein:
the lens is a unitary lens,
the viewing axis is a first viewing axis,
the one eye is a first eye,
the unitary lens is configured to be supported in a path of a straight ahead line of sight forming a center axis of a second eye of the typical wearer,
a second viewing axis extends from the second eye and the center axis of the second eye at an angle from the center axis of the second eye away from the typical wearer's nose in a direction opposite that of the first viewing axis measured along the horizontal meridian of the rear surface,
each point of a second set of points along the horizontal meridian of the rear surface is associated with an angle of the second viewing axis where the second viewing axis intersects the each point of the second set of points, and
the prismatic power of the lens does not exceed approximately 0.23 diopter for every point of the second set of points at angles of the second viewing axis along the horizontal meridian of the rear surface from 0 degrees to approximately 30 degrees.

19. The lens of claim 15, wherein the prismatic power of the lens does not exceed approximately 0.6 diopter for every point along the horizontal meridian of the rear surface at angles of the viewing axis from greater than approximately 30 degrees to approximately 55 degrees.

20. The lens of claim 15, wherein the prismatic power of the lens increases at an average rate not exceeding approximately 0.01 diopter per degree of increasing angle of the viewing axis throughout points along the horizontal meridian of the rear surface associated with angles of the viewing axis from approximately 30 degrees to approximately 40 degrees.

* * * * *

UNITED STATES PATENT AND TRADEMARK OFFICE
CERTIFICATE OF CORRECTION

PATENT NO. : 11,977,277 B2
APPLICATION NO. : 17/728722
DATED : May 7, 2024
INVENTOR(S) : Robinson et al.

Page 1 of 1

It is certified that error appears in the above-identified patent and that said Letters Patent is hereby corrected as shown below:

In the Specification

In Column 7, Line 21, delete "Ox," and insert -- $\theta_X$, --, therefor.

In Column 7, Line 23, delete "BY," and insert -- $\theta_Y$, --, therefor.

Signed and Sealed this
Eleventh Day of March, 2025

Coke Morgan Stewart
*Acting Director of the United States Patent and Trademark Office*